(12) United States Patent
Zelen et al.

(10) Patent No.: US 10,869,949 B2
(45) Date of Patent: Dec. 22, 2020

(54) METHOD FOR TREATING SUBJECTS SUFFERING FROM CHRONIC ULCERS

(71) Applicants: Geistlich Pharma AG, Wolhusen (CH); University of Southern California, Los Angeles, CA (US)

(72) Inventors: Charles Zelen, Roanoke, VA (US); David Armstrong, Los Angeles, CA (US); Paul Glat, Conshohocken, PA (US); Jarrod Kaufman, Brick, NJ (US); Marco Mehr, Willisau (CH); Lothar Schloesser, Lucerne (CH); Mark Spilker, Kilchberg (CH)

(73) Assignees: Geistlich Pharma AG, Wolhusen (CH); University of Southern California, Los Angeles, CA (US)

( * ) Notice: Subject to any disclaimer, the term of this patent is extended or adjusted under 35 U.S.C. 154(b) by 0 days.

(21) Appl. No.: 16/845,633

(22) Filed: Apr. 10, 2020

(65) Prior Publication Data
US 2020/0324020 A1    Oct. 15, 2020

Related U.S. Application Data

(60) Provisional application No. 62/832,417, filed on Apr. 11, 2019.

(51) Int. Cl.
| | | |
|---|---|---|
| *A61L 27/24* | (2006.01) | |
| *A61L 27/44* | (2006.01) | |
| *A61L 27/54* | (2006.01) | |
| *A61L 27/38* | (2006.01) | |
| *A61P 17/02* | (2006.01) | |
| *A61L 27/56* | (2006.01) | |

(52) U.S. Cl.
CPC .......... *A61L 27/24* (2013.01); *A61L 27/3808* (2013.01); *A61L 27/44* (2013.01); *A61L 27/54* (2013.01); *A61L 27/56* (2013.01); *A61P 17/02* (2018.01); *A61L 2300/414* (2013.01)

(58) Field of Classification Search
CPC .......... A61L 27/24; A61L 27/56; A61P 17/02
See application file for complete search history.

(56) References Cited

U.S. PATENT DOCUMENTS

| | | | |
|---|---|---|---|
| 5,837,278 A | 11/1998 | Geistlich et al. | |
| 6,713,085 B2 | 3/2004 | Geistlich et al. | |
| 2002/0160036 A1* | 10/2002 | Geistlich | A61L 31/044 424/443 |
| 2005/0021141 A1* | 1/2005 | Bleyer | A61L 15/40 623/15.12 |
| 2011/0270394 A1* | 11/2011 | Herford | A61L 31/146 623/15.12 |

FOREIGN PATENT DOCUMENTS

| | | |
|---|---|---|
| EP | 1252903 B1 | 11/2006 |
| EP | 1709981 B1 | 3/2010 |

OTHER PUBLICATIONS

Seal et al (Wound Management and Prevention, 2018, vol. 64, pp. 8-10) (Year: 2018).*
Kalani et al (Diabetes Care, 1999, vol. 22, pp. 147-151) (Year: 1999).*
Sood et al (Advances in Wound Care (New Rochelle), 2014, vol. 3, pp. 511-529) (Year: 2014).*
Advanced Tissue (How to Remove Wound Care Products When Changing Dressings, Jun. 13, 2014, https://advancedtissue.com/2014/06/remove-wound-care-products-changing-dressings/ ) (Year: 2014).*
Chattopadhyay et al (Biopolymers, Aug. 2014, vol. 101, pp. 821-833) (Year: 2014).*
Krishnaswamy, et al. "Matrix metalloproteinases: The sculptors of chronic cutaneous wounds", Biochimica et Biophysica Acta (BBA)— Molecular Cell Research, vol. 1864, Issue 11, Part B, Nov. 2017, pp. 2220-2227.
Geistlich Derma-GideTM Instructions for Use, Nov. 2018, 1 page.
Demidova-Rice, "Acute and Impaired Wound Healing: Pathophysiology and Current Methods for Drug Delivery, Part 1: Normal and Chronic Wounds: Biology, Causes, and Approaches to Care", Adv., Skin Wound Care, 2012, 25(7): 304-314.
Frykberg and Banks, "Challenges in the Treatment of Chronic Wounds", Advances in Wound Care, 2015, vol. 4(9), 560-582.
Han and Ceilley, "Chronic Wound Healing: A Review of Current Management and Treatments". Adv. Ther., 2017, 34:599-610.
Lorenz et al., "Expansion of the peri-implant attached gingiva with a three-dimensional collagen matrix in head and neck cancer patients-results from a prospective clinical and histological study.", Clin. Oral Invest. (2017), 21:1103-1111.

* cited by examiner

*Primary Examiner* — Mark V Stevens
(74) *Attorney, Agent, or Firm* — Rothwell, Figg, Ernst & Manbeck, P.C.

(57) ABSTRACT

A method, material, and kit for promoting neutrophils and monocytes to localize at a chronic ulcer site, promoting formation of a multi-layered cell structure in the ulcer site, promoting conversion of monocytes to macrophages, promoting secretion of the patient's own growth factors, promoting tissue proliferation and cell migration, promoting production and cross-linking of collagen at the chronic ulcer site, promoting growth of endothelial cells, promoting angiogenesis that was stalled at the chronic ulcer site, promoting formation of a vascular network and granulation, promoting oxygenation of the chronic ulcer site, and reducing one or more of purulent drainage, erythema, pain, warming, tenderness, induration, and bleeding at the chronic ulcer site.

30 Claims, 18 Drawing Sheets

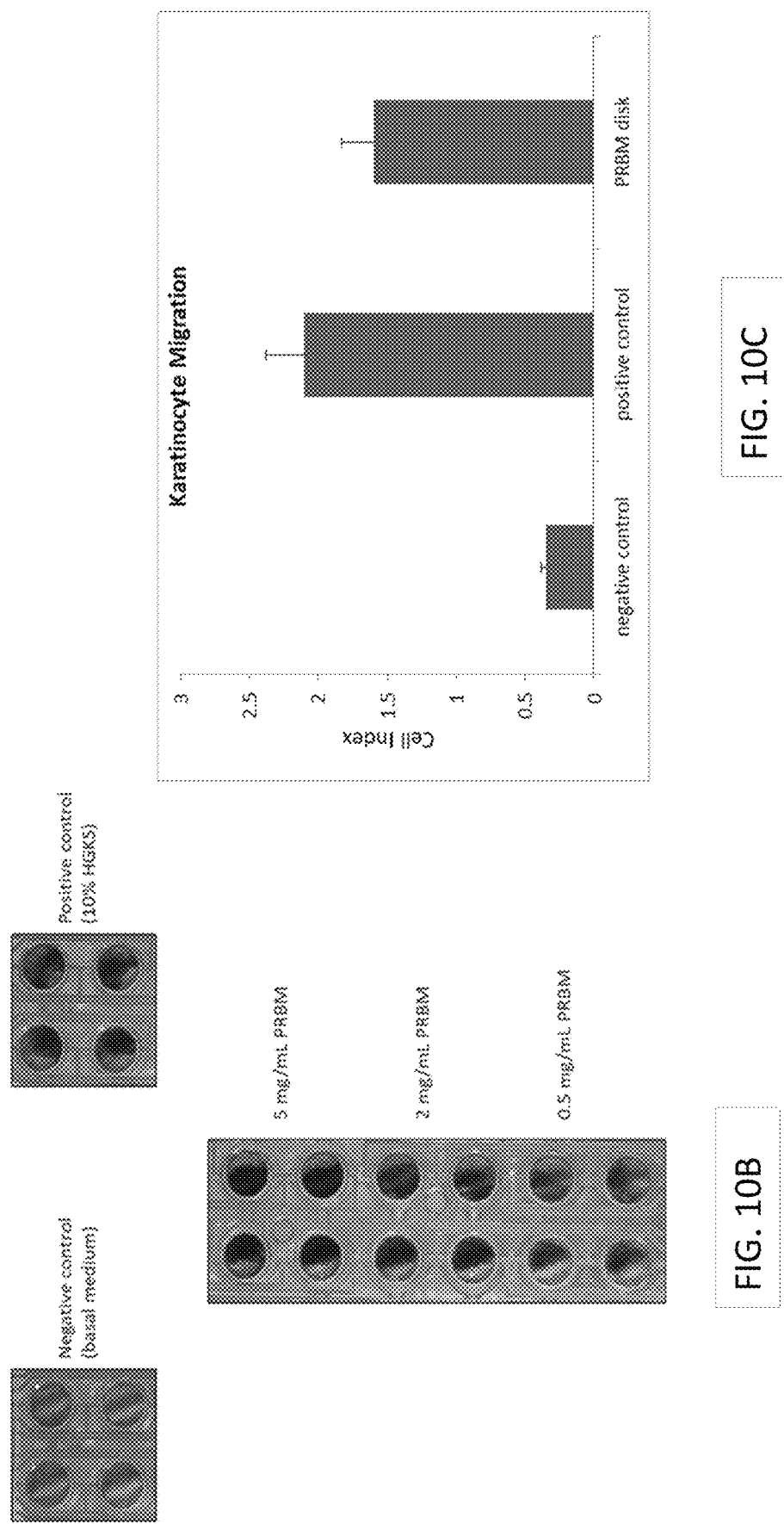

METHOD FOR TREATING SUBJECTS SUFFERING FROM CHRONIC ULCERS

CROSS-REFERENCE TO RELATED APPLICATIONS

This application claims priority benefit of U.S. provisional application No. 62/832,417, filed Apr. 11, 2019, the disclosures of which are incorporated herein by reference in their entireties.

FIELD OF THE DISCLOSURE

This disclosure relates to methods and materials for treating subjects suffering from chronic ulcers, in particular chronic skin ulcers.

BACKGROUND

Chronic ulcers are persistent, non-healing or slow-healing ulcers affecting millions of persons each year, particularly the elderly and diabetics. Wounds that fail to progress through the healing process in a timely manner, e.g. 4-5 weeks, are often referred to as chronic ulcers. Such ulcers may last months or years, recur in a majority of patients, can lead to loss of function and decreased quality of life, and are a significant cause of morbidity. Some common features shared by each of these ulcers include prolonged or excessive inflammation, persistent infections, formation of drug-resistant microbial biofilm and the inability of dermal and/or epidermal cells to respond to reparative stimuli.

As explained by Frykberg and Banks (Advances in Wound Care, 2015, Vol. 4(9), 560-582), which is incorporated herein by reference in its entirety, the healing process of wounds is highly complex and is dependent on an intricate interplay between numerous factors working in concert to restore injured skin towards repaired barrier function. Chronic ulcers are different from acute wounds, which progress in an ordered and timely manner through four temporarily and spatially overlapping phases: hemostasis, inflammation, proliferation and remodeling. In contrast to acute wounds, chronic ulcers often stall in the inflammation phase of healing. Despite differences in etiology at the molecular level, chronic ulcers share certain common features, including excessive levels of pro-inflammatory cytokines, proteases, reactive oxygen species (ROS), reactive nitrogen species (RNS) and senescent cells, as well as the existence of persistent infection, and a deficiency of stem cells that are often also dysfunctional. Due to repeated tissue injury, microorganisms and platelet-derived factors, such as transforming growth factor-$\beta$ (TGF-$\beta$) or extracellular matrix (ECM) fragment molecules, stimulate the constant influx of immune cells; the pro-inflammatory cytokine cascade therefore becomes amplified and persists for a prolonged time, leading to elevated levels of proteases. In chronic ulcers, protease levels exceed those of their respective inhibitors, leading to destruction of ECM and degradation of growth factors and their receptors. The proteolytic destruction of ECM not only prevents the ulcer from moving forward into the proliferative phase, but also attracts more inflammatory cells, thus amplifying the inflammation cycle.

As discussed in Demidova-Rice (Adv. Skin Wound Care, 2012, 25(7): 304-314), which is incorporated herein by reference in its entirety, chronic ulcers often feature persistent infections, formation of drug-resistant microbial biofilms, and the inability of dermal and/or epidermal cells to respond to reparative stimuli. In aggregate, these pathophysiologic phenomena result in the failure of these ulcers to heal in contrast to acute wounds, which heal within a normal period of time.

Venous ulcers display profound pathological changes that arise secondary to venous valvular incompetence in the deep and superficial veins. This, in turn, leads to a constant blood backflow resulting in an increase in venous pressure. Pressure-induced changes in blood vessel wall permeability then lead to leakage of fibrin and other plasma components into the perivascular space. Accumulation of fibrin has direct and negative effects on wound healing. It down-regulates collagen synthesis, leads to formation of pericapillary fibrin cuffs that create a barrier for normal vessel function, and traps blood-derived growth factors. Using confocal microscopy, it has been demonstrated that fibrin deposits surrounding dermal veins are patch-like and discontinuous. This finding questions the barrier role of fibrin cuffs and suggests the presence of other yet unknown factors contributing to low oxygen tension found in venous ulcers and surrounding tissues. Identification of these factors may reveal novel targets for therapeutic interventions and treatment of venous ulcers.

Arterial ulcers occur because of arterial insufficiency caused by atherosclerosis or embolism that can lead to narrowing of arterial lumen and ischemia, which prevents timely healing of minor traumatic injuries. Unlike venous ulcers, which generally arise between the knee and the ankle, arterial leg wounds may present at any spot distal to arterial perfusion such as a tip of a toe.

Pressure ulcers develop as a result of prolonged unrelieved pressure and shearing force applied to skin and the underlying muscle tissue leading to a decrease in oxygen tension, ischemia reperfusion injury, and tissue necrosis. Pressure ulcers are common in patients with compromised mobility and decreased sensory perception (neuropathies) and are exacerbated in individuals with arterial and venous insufficiencies.

Other abnormalities leading to development of chronic ulcers in diabetic patients (also called diabetic foot ulcers) include polyneuropathy, often linked to vascular impairment, deficiencies in muscle metabolism, and a number of microvascular pathologies often caused by hyperglycemia. Macroscopic pathologies seen in chronic, particularly diabetic, ulcers often are linked to cellular phenotypic abnormalities, including low mitogenic/motogenic potential and inability to respond to environmental cues.

Although chronic ulcers described in the present disclosure may have different origins, each ulcer is characterized by a chronically inflamed wound bed and a failure to heal. Excessive recruitment of inflammatory cells often triggered by infection and cell extravasation is facilitated by disproportionate expression of vascular cell adhesion molecule 1 and interstitial cell adhesion molecule 1 by resident endothelial cells Inflammatory cells accumulated inside the chronic ulcer produce various ROS that damage structural elements of the ECM and cell membranes and lead to premature cell senescence. In addition to these direct negative effects, ROS together with pro-inflammatory cytokines induce production of serine proteinases and matrix metalloproteinases (MMPs) that degrade and inactivate components of the ECM and growth factors necessary for normal cell function. Inactivation of proteinase inhibitors by proteolytic degradation augments this process. Therefore, although the production of growth factors is often increased in chronic compared with acute wounds, their quantity and bio-availability are significantly decreased.

Since chronic ulcers are portals for local and systemic infection, chronic ulcers can have particularly devastating effects for patients. Poor healing rates of chronic ulcers with conventional therapies are believed to be due to the inadequacy of conventional therapies to promote sufficient migration and proliferation of regenerating cells, chemokines, cytokines, nutrients, and growth factors to the site of the ulcer. Vasculopathy and infection lead to chronic inflammation at the ulcer site, which is associated with an imbalance of growth factors and proteases coupled with reduced proliferation and migration of cells. Increased MMPs at chronic ulcer sites inhibits growth factors, which leads to decreased migration, attraction and proliferation of fibroblasts, keratinocytes and endothelial cells into the ulcer site for healing.

While protease digestion of ECM components facilitates cell migration and proliferation and plays a role in the regulation of inflammatory processes, over-expression of proteases and increased protease concentrations are associated with chronic ulcers. MMPs are a large family of closely related zinc-finger proteases that digest ECM components including collagens, fibronectin, laminin, and proteoglycans. In normal healing processes, the proteolytic activities of MMPs and neutrophil elastase (NE) are maintained by endogenous protease inhibitors, including tissue inhibitors of matrix metalloproteinases (TIMPs), $\alpha$2-macroglobin, and al-proteinase inhibitor. Chronic ulcers involve elevated concentrations of proteases and increased protease expression relative to acute wounds, and the increased concentration contributes to the stalled healing and digestion of the ECM resulting in a stalled inflammatory phase. Related degradation of the structural and adhesion proteins, growth factors, and growth factor receptors also stall healing.

Diabetes is a major cause of non-traumatic amputations. Chronic skin ulcers, particularly diabetic leg and foot ulcers are a major source of morbidity in persons with diabetes. Ulceration, infection, gangrene, and amputation are the significant complications of the disease, estimated to cost many billions of dollars each year (estimated at $50 billion per year in the United States alone) and affect hundreds of millions of people worldwide. The four most common types of chronic ulcers are: venous ulcers, arterial ulcers, diabetic ulcers, and decubitus (pressure) ulcers. Infections are common in diabetic patients and are often more severe than infections found in non-diabetic patients. Persons with diabetes have an increased risk of developing an infection of any kind, resulting in poor quality of life and risk of limb amputation.

Care for chronic ulcers has been reported to cost 2% to 3% of healthcare budgets in developed countries. While various wound care products have been used for treating normally healing wounds and acute ulcers, there is a demonstrable lack of evidence demonstrating efficacy for a majority of existing wound care products for treating chronic ulcers.

As discussed in Han and Ceilley (Adv. Ther., 2017, 34:599-610), which is incorporated herein by reference in its entirety, in addition to lack of efficacy, existing graft materials have disadvantages, including high expense, difficulty in handling, delicacy or difficulty in obtaining graft material, poor adhesion to the ulcer bed, require fenestration, require silicone layers as barrier layers, cannot be combined with vacuum assisted closure (VAC) therapy, and fail to sufficiently reduce ulcer area, fail to heal all ulcers, fail to promote formation of sufficient granulation tissue, or fail to reduce ulcer area at an acceptable closure rate. Further, there is a need for products that can provide a hemostatic effect in chronic ulcers. Promoting blood clotting is particularly important for patients treated with anticoagulants.

For example, one conventional advanced wound care product, EpiFix® (MiMedx®), is an amniotic membrane allograft made of dehydrated human amnion/chorion membrane tissue (dHACM). The tissue is derived from donated human amniotic membranes and, as such, is difficult to handle during surgery as well as being very expensive. Further, it has been observed that amniotic tissue products such as EpiFix® often float on the blood in the treatment site and lack a hemostatic effect.

Available membranes and products have been found to induce different cellular inflammatory responses after implantation. In the highly complex chronic ulcer environment, it is unpredictable how a given wound care product will affect physiological processes after implantation. To date, existing products have demonstrated high failure rates against chronic ulcers and there is a demonstrable lack of efficacy due to the complexity, intractability and unpredictability of the stalled healing process in chronic ulcers. Thus, despite the prevalence of chronic ulcers, and the availability of graft materials, there exists a need for a method of healing chronic ulcers using a relatively inexpensive, lightweight, easy-to-handle material that can facilitate successful healing of the ulcerated area.

U.S. Pat. No. 6,713,085 and European Patent No. 1,709, 981 disclose a multilayer sheet of collagen material comprising (i) a barrier layer of collagen material having a smooth face and a rough fibrous face opposite said smooth face and (ii) a (spongeous) spongeous matrix layer of collagen material connected ("adhered") to said fibrous face, said spongeous matrix layer of collagen material having an open "sponge-like" texture, and teach that this multilayer sheet of collagen material can be used as a substitute of autologous graft for free mucosal grafts or split thickness skin grafts (see U.S. Pat. No. 6,713,085, C6, lines 16-17). That multilayer sheet of collagen material has been marketed under the trademark Geistlich Mucograft® as a unique collagen matrix for soft tissue regeneration in the dental field especially for gain of keratinized tissue and for recession coverage. That multilayer sheet of collagen material has also been used by Ghanaati et al. for augmentation around dental implants in patients with former head and neck cancer (see Clin. Oral Invest. (2017), 21:1103-1111) and regeneration of facial surgical wounds to after skin cancer removal (see J. Cell Commun. Signal. (2016) 10:3-15).

Soft tissue regeneration in the dental field and regeneration of oral or facial surgical wounds after skin cancer removal involves normal healing processes of acute wounds: it is pathophysiologically quite different from treatment of chronic ulcers. As taught by the various above references incorporated herein by reference, due to the distinct pathophysiology of chronic ulcers, products that are effectively used to treat acute wounds indeed typically fail to treat chronic ulcers due to the different physiological phenomena contributing to the chronicity of chronic ulcers.

SUMMARY OF THE INVENTION

The present disclosure includes methods of treating a subject suffering from chronic ulcers, notably chronic skin ulcers, by increasing liquid uptake capacity, promoting blood clot formation, promoting a hemostatic effect and accelerating blood coagulation, attracting cells, promoting cell attachment and cell growth of human dermal fibroblasts, human epidermal keratinocytes, human endothelial cells, and human pluripotent stem cells, binding and preserving the subject's own growth factors, inhibiting matrix metalloproteinases (MMPs) and other collagenases, restoring the tensile strength of skin at the chronic ulcer site to at least 70% of its original tensile strength, restoring tissue notably skin at the chronic ulcer site to color, sheen, and tension of the patient's skin, or a combination thereof at a chronic ulcer site of the subject.

In some aspects, the subject suffers from venous ulcers, vascular ulcers, arterial ulcers, diabetic ulcers, and decubitus (pressure) ulcers, peripheral vascular disease, cellulitis, osteomyelitis, ulcers at surgical sites including donor sites, graft sites, Mohs surgery sites, laser surgery sites, podiatric surgical sites, dehiscence, or a combination thereof. In some aspects, the subject suffers from venous leg ulcers, diabetic foot ulcers, pressure ulcers, or a combination thereof. In some aspects, the subject suffers from diabetic foot ulcers (DFU). In some aspects, the subject suffers from venous leg ulcers (VLU).

In some aspects, the subject requires ulcer dressing changes, e.g., daily, every other day, every three days, every five days or every week.

In some aspects, the subject suffers from diabetes, metabolic disorders, thyroid malfunction or dysfunction, and/or an autoimmune disease. In some aspects, the subject suffers from hyperglycemia, polyneuropathy (e.g. peripheral sensory neuropathy), vasculopathy, infection, fibrin cuff, and/or venous hypertension. In some aspects, the subject has been or is being treated with corticosteroid therapy, is undergoing radiation therapy, is receiving anti-coagulation therapy, chemotherapy, or uses drugs, alcohol, tobacco, or other agents that disrupt the normal healing process.

In some aspects, the subject treated according to the method of the present disclosure is also treated with compression therapy, vacuum assisted closure (VAC), offloading, negative pressure, hyperbaric oxygen therapy, or a combination thereof. Compression therapy may include therapeutic compression stockings, multilayer compression wraps, wrapping the foot and/or leg with an ACE bandage or dressing, or compression boot.

In some aspects, the present disclosure provides a method of treating a chronic ulcer in a subject in need thereof comprising
i) cleaning to remove bacteria and other pathogens and/or debriding the chronic ulcer until the edges of the ulcer contain viable tissue;
ii) aseptically implanting into the chronic ulcer of the subject a multilayer sheet of collagen material in dry state comprising (i) a barrier layer of collagen material having a smooth face and a rough fibrous face opposite said smooth face and (ii) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer;
iii) hydrating the implanted multilayer sheet of collagen material in dry state, generally using blood, a sterile isotonic solution, such as e.g. a sterile saline solution, or a combination thereof; and
iv) providing a dressing over the implanted, hydrated multilayer sheet of collagen material, thereby restarting stalled cell migration, proliferation and angiogenesis at the chronic ulcer site.

The term "in a dry state" for the multilayer sheet of collagen material means here that the multilayer sheet of collagen material has a water content of 5-20% as determined by Karl-Fischer titration according to Ph. Eur. 2.5.12A, USP <921>, which is incorporated herein by reference in its entirety.

The term "barrier" in "barrier layer of collagen material" refers to the property of the smooth side of inhibiting direct cell migration through the collagen material as described in U.S. Pat. No. 5,837,278, which is referred to in Example 2 of U.S. Pat. No. 6,713,085 and European Patent No. 1'709'981.

The term "collagen material" here means a collagen-based material which comprises 70-100% (w/w) collagen and 0-70% (w/w) elastin. The elastin content is here measured by desmosine/iodesmosine determination according to a modification of a known method involving hydrolysis and RP-HPLC (see e.g. Guida E. et al. 1990 *Development and validation of a high performance chromatography method for the determination of desmosines in tissues* in Journal of Chromatography or Rodriguqe P 2008 *Quantification of Mouse Lung Elastin During Prenatal Development* in The Open Respiratory Medicine Journal). To determine the desmosine/isodesmosine content of dry elastin, the elastin of the collagen material is subjected to elastin isolation procedures as described by Starcher and Galione in 1976 (*Purification and Comparison of Elastin from Different Animal Species* in Analytical Biochemistry). That collagen material is suitably derived from tissues of natural origin which contain such proportions of collagen and elastin. Examples of such tissues include vertebrate, in particular mammalian (e.g. porcine, bovine, equine, ovine, caprine, lapine) peritoneum or pericardium membrane, placenta membrane, small intestine submucosa (SIS), dermis, dura mater, ligaments, tendons, thoracic diaphragm, omentum, fascie of muscles or organs.

In the present specification the shorter term "fibrous face of the multilayer sheet of collagen material" may be used to designate the "rough fibrous face of said barrier layer of collagen material to which is connected said spongeous matrix layer of collagen material having an open sponge-like texture".

As taught in U.S. Pat. No. 6,713,085, European Patent No. 1'709'981 (Geistlich, Schlösser and Boyne), notably in Example 3, and U.S. Pat. No. 5,837,278 (Geistlich, Eckmayer and Boyne), the disclosures of which is incorporated herein by reference in their entireties, as well as the present specification:

the barrier layer of collagen material (i) having a smooth face and a rough fibrous face opposite said smooth face of the multilayer sheet of collagen material, may derived from a natural collagen membrane, notably a mammalian, in particular bovine, porcine or ovine, peritoneum, pericardium, placenta or basal membrane. That collagen of the barrier layer of collagen material is usually predominantly collagen I, collagen III or a mixture thereof. One suitable material for that barrier layer of collagen material (i) is the resorbable porcine bilayer membrane Geistlich Bio-Gide® available from Geistlich Pharma AG, Switzerland.

The collagen of the spongeous matrix layer of collagen material (ii) connected to said rough fibrous face that has an open sponge-like texture of the multilayer sheet of collagen material, may be formed of collagen I, II, III, IV or VII or any combination of those collagen types. The collagen of spongeous matrix layer of collagen material (ii) is usually predominantly formed of collagen I, collagen III or a combination thereof, e.g. about 87% collagen I and 13% collagen III.

The spongeous matrix layer (ii) of collagen material connected to said rough fibrous face that has an open sponge-like texture of the multilayer sheet of collagen material, is usually obtained by applying a collagen slurry to the rough fibrous face of the barrier layer of collagen material (i) and freeze-drying the combined product.

The multilayer sheet of collagen material has a thickness of about 0.5-25 mm.

In some aspects, the multilayer sheet of collagen material of the present disclosure has properties such that it allows gaseous exchange at the chronic ulcer site sufficient to promote healing of the chronic ulcer, infiltration of white blood cells, enzymes, cytokines, and growth factors beneficial for restarting stalled healing.

In some aspects, the present disclosure includes a method for promoting autolytic debridement of the chronic ulcer.

In some aspects, the chronic ulcer extends at least through the dermis and has been present for greater than 4 weeks. In some aspects, the chronic ulcer extends at least through the hypodermis and has been present for greater than 6 weeks. In some aspects, the chronic ulcer has been present for greater than 8, 10, 12, 24 or 40 weeks.

In some aspects, the method further comprises applying a secondary dressing or re-dressing the chronic ulcer after step iv) is performed.

In some aspects, the method further comprises applying sterile saline to remove a dressing material from the multilayer sheet of collagen material after step iv) is performed.

In some aspects, the method further comprises changing the dressing over the implanted multilayer sheet of collagen material every 1 to 7 days after step iv) is performed.

In some aspects, the method further comprises removing exudate from the chronic ulcer site every 1 to 7 days after step iv) is performed.

In some aspects, the method further comprises inspecting the chronic ulcer every 1 to 7 days, in particular every week, after step iv) and removing the dressing after a first visible epithelialization is observed at the chronic ulcer or removing the implanted multilayer sheet of collagen material and repeating steps i) to iv) if one or more of redness, swelling, hematomas, blistering, inflammation, excess exudate, infection, and necrosis are observed at the chronic ulcer.

In some aspects, the method further comprises performing one or more of toe-blood pressure readings, pulse volume recordings, transcutaneous oxygen measurements, and skin perfusion pressure measurements.

In some aspects, the method further comprises one or more of promoting neutrophils and monocytes to localize at the chronic ulcer site, promoting formation of a multi-layered cell structure in the ulcer site, promoting conversion of monocytes to macrophages, promoting secretion of the patient's own growth factors, promoting tissue proliferation and cell migration, promoting production and cross-linking of collagen at the chronic ulcer site, promoting growth of endothelial cells, promoting angiogenesis that was stalled at the chronic ulcer site, promoting formation of a vascular network and granulation, promoting oxygenation of the chronic ulcer site, and reducing one or more of purulent drainage, erythema, pain, warming, tenderness, induration, and bleeding at the chronic ulcer site.

In some aspects, the present disclosure provides a method for increasing liquid uptake capacity in a chronic ulcer of a subject in need thereof, by aseptically implanting into the chronic ulcer of the subject a multilayer sheet of collagen material in dry state comprising (i) a barrier layer of collagen material having a smooth face and a rough fibrous face opposite said smooth face and (ii) a spongeous matrix layer of collagen material connected to said rough fibrous face, said spongeous matrix layer of collagen material having an open sponge-like texture, such that said rough fibrous face of the barrier layer to which is connected that spongeous matrix layer of collagen material having an open sponge-like texture faces toward and is adjacent to the bed of the chronic ulcer; and hydrating the implanted multilayer sheet of collagen material, thereby increasing liquid uptake capacity in the chronic ulcer. In some aspects, exudate drainage and bleeding from the chronic ulcer are inhibited, and floating away of the multilayer sheet of collagen material out of the bed of the chronic ulcer is prevented, the multilayer sheet of collagen material sticking to the bed of the chronic ulcer, probably due to capillary forces and its high pliability and conformability to uneven surfaces.

In some aspects, the present disclosure provides a method for promoting hemostasis in a chronic ulcer of a subject in need thereof, by aseptically implanting a multilayer sheet of collagen material in dry state comprising (i) a barrier layer of collagen material having a smooth face and a rough fibrous face opposite said smooth face and (ii) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer, and hydrating the implanted multilayer sheet of collagen material, thereby promoting hemostasis in the chronic ulcer. In some aspects, blood clot formation in a chronic ulcer is accelerated by at least 1.5- to 4-fold, 2-fold, 2.5-fold, 3-fold, or 3.5-fold, compared to blood clot formation in a chronic ulcer in the absence of said implanted multilayer sheet of collagen material. In some aspects, blood clot formation in a chronic ulcer is accelerated by at least 1.5- to 4-fold, 2-fold, 2.5-fold, 3-fold, or 3.5-fold, compared to blood clot formation in a chronic ulcer in the absence of said implanted multilayer sheet of collagen material for a subject receiving anti-coagulation therapy. In some aspects, the present disclosure provides a method for promoting uptake of red and white blood cells into the matrix of the multilayer sheet of collagen material of the present disclosure.

In some aspects, the present disclosure provides a method for binding and preserving a subject's own growth factors in a chronic skin ulcer of a subject in need thereof, by aseptically implanting into the chronic ulcer of the subject a multilayer sheet of collagen material in dry state comprising (i) a barrier layer of collagen material having a smooth face and a rough fibrous face opposite said smooth face and (ii) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic skin ulcer; and hydrating the implanted multilayer sheet of collagen material, thereby promoting binding of said subject's own growth factors with the multilayer sheet of collagen material and preservation of said subject's own growth factors and growth factor activity in the chronic skin ulcer, thereby inducing expression of one or more growth factor-responsive genes in human dermal fibroblasts, human epidermal keratinocytes, human endothelial cells, and human pluripotent stem cells in the chronic skin ulcer of the subject, and promoting cell growth of one or more human cell types in the chronic skin ulcer.

In some aspects, the growth factors are two or more of transforming growth factors (TGFs), fibroblast growth factors (FGFs), epidermal growth factor (EGF), Insulin-like Growth Factor (IGF-1), Platelet-derived Growth Factors (PDGFs), and vascular endothelial growth factors (VEGFs).

In some aspects, said one or more human cell types are human fibroblasts, epidermal keratinocytes, endothelial cells, and pluripotent stem cells.

In some aspects, the present disclosure provides a method for attracting one or more human cell types to a chronic skin ulcer of a subject in need thereof, comprising
i) aseptically implanting into the chronic skin ulcer of the subject a multilayer sheet of collagen material in a dry state comprising (i) a barrier layer of collagen material having a smooth face and a rough fibrous face opposite said smooth face and (ii) a layer of collagen material connected to said rough fibrous face, said layer of collagen material having an open sponge-like texture, such that said rough fibrous collagen face of said matrix to which is connected the layer of collagen material having an open sponge-like texture faces toward and is adjacent to the bed of the chronic skin ulcer, and
(ii) hydrating the implanted multilayer sheet of collagen material, thereby attracting one or more human cell types to the chronic skin ulcer.

In some aspects, said one or more human cell types are human dermal fibroblasts, epidermal keratinocytes, endothelial cells, and human pluripotent stem cells.

In some aspects, the present disclosure provides a method for promoting attachment and growth of one or more human cell types in a chronic skin ulcer of a subject in need thereof, by
(i) aseptically implanting into the chronic ulcer of the subject a multilayer sheet of collagen material in dry state comprising (i) a barrier layer of collagen material having a smooth face and a rough fibrous face opposite said smooth face and (ii) a matrix layer of collagen material connected to said rough fibrous face, said spongeous matrix layer of collagen material having an open sponge-like texture, such that the rough face of the barrier layer of collagen material to which is connected that spongeous matrix layer of collagen material having an open sponge-like texture faces toward and is adjacent to the bed of the chronic skin ulcer,
(ii) hydrating the implanted multilayer sheet of collagen material in dry state,
(iii) promoting attachment and growth of one or more human cell types in the chronic skin ulcer, and
(iv) promoting proliferation of one or more human cell types in the chronic skin ulcer.

In some aspects, said one or more human cell types are human dermal fibroblasts, epidermal keratinocytes, endothelial cells, and human pluripotent stem cells.

In some aspects, the present disclosure provides a method for inhibiting one or more MMPs in a chronic skin ulcer of a subject in need thereof, by aseptically implanting into the chronic ulcer of the subject a multilayer sheet of collagen material in a dry state comprising (i) a barrier layer of collagen material having a smooth face and a rough fibrous face opposite said smooth face and (ii) a layer of collagen material connected to said rough fibrous face, said layer of collagen material having an open sponge-like texture, such that said rough fibrous collagen face of said matrix to which is connected the layer of collagen material having an open sponge-like texture faces toward and is adjacent to the bed of the chronic skin ulcer and hydrating the implanted multilayer sheet of collagen material, thereby inhibiting MMPs and other collagenases in the chronic skin ulcer.

In some aspects, said MMPs are MMP-1, MMP-2, MMP-3, MMP-8, and MMP-9 or any combination of those MMP types.

In some aspects, the present disclosure provides a method for producing a kit including a blister, a pouch, a multilayer sheet of collagen material of the present disclosure in the blister, and instructions for use of the multilayer sheet of collagen material of the present disclosure, wherein the instructions for use require a user to take specific actions including a plurality of the following: aseptically trimming the multilayer sheet of collagen material to the desired size and/or shape to form an implant; using a scalpel, shears, scissors, and/or graspers to trim and/or shape the multilayer sheet of collagen material to form an implant; applying the multilayer sheet of collagen material to the chronic ulcer site with the spongeous layer facing the chronic ulcer; directly applying the multilayer sheet of collagen material to the chronic ulcer site in a dry state; storing the multilayer sheet of collagen material at a temperature of between about 10 to about 30° C. prior to the implanting step; implanting the multilayer sheet of collagen material in the chronic ulcer and then completely hydrating the multilayer sheet of collagen material in situ using blood, sterile saline solution, or a combination thereof to hydrate the multilayer sheet of collagen material; applying a first dressing that covers the chronic ulcer site having the multilayer sheet of collagen material implanted therein. In some aspects, the kit further comprises instructions for use requiring a user to take further specific actions including a plurality of the following: providing a hydrocolloid dressing over the chronic ulcer site having the multilayer sheet of collagen material implanted therein; applying a secondary dressing or re-dressing the chronic ulcer site; applying a non-adhesive secondary dressing or re-dressing; applying sterile saline to remove a dressing material from the multilayer sheet of collagen material; changing the dressing over the implanted multilayer sheet of collagen material every 1 to 7 days, in particular every week, after implantation; changing the secondary dressing over the first dressing every 1 to 7 days after implantation; removing exudate from the chronic ulcer site every 1 to 7 days after implantation; monitoring the size, shape, color, inflammation, and drainage of the edges of the chronic ulcer site every 1 to 7 days after implantation; removing the implanted multilayer sheet of collagen material and repeating the implanting step; ensuring that the chronic ulcer site is free of acute infection before implanting the multilayer sheet of collagen material; treating infections at or near the chronic ulcer site prior to implanting the multilayer sheet of collagen material; identifying patients with allergies or sensitivities to porcine or collagen materials prior to implanting the multilayer sheet of collagen material; and not implanting the multilayer sheet of collagen material in patients that have allergies or sensitivities to porcine or collagen materials.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various exemplary and non-limiting aspects of the subject matter of this disclosure. In the drawings, like reference numbers indicate identical or functionally similar elements.

FIG. 10B shows the effect of extracts of extracts of the multilayer sheet of collagen material on epidermal keratinocyte trans-well migration. FIG. 10C shows the effect of the multilayer sheet of collagen material (disk) on epidermal keratinocyte trans-well migration.

DETAILED DESCRIPTION

Figure 1:
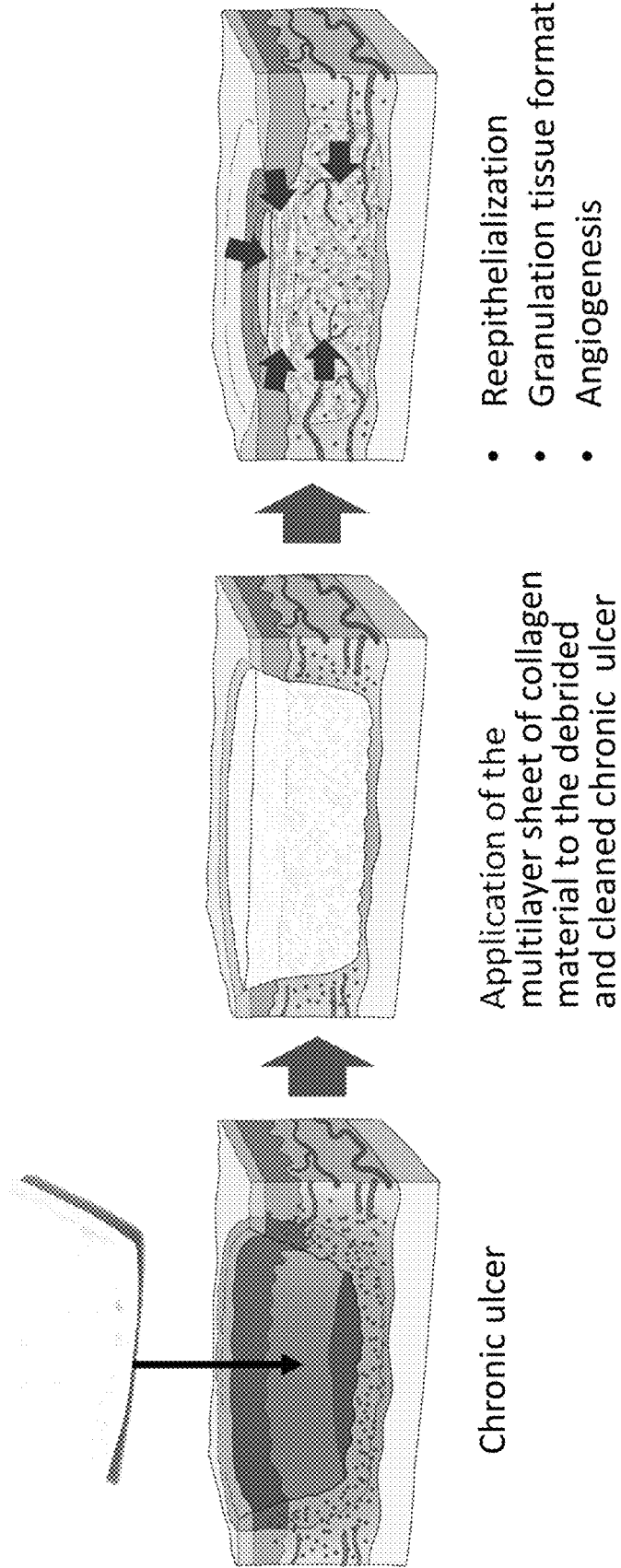
FIG. 1 is a schematic view of a multilayer sheet of collagen material according to one aspect of the present disclosure implanted in a chronic ulcer site and the healing process effected thereby.

While aspects of the subject matter of the present disclosure may be embodied in a variety of forms, the following description and accompanying figures are merely intended to disclose some of these forms as specific examples of the subject matter encompassed by the present disclosure. Accordingly, the subject matter of this disclosure is not intended to be limited to the forms or embodiments so described and illustrated.

The physiological process of normal wound healing is achieved through four temporarily and spatially overlapping phases: hemostasis, inflammation, proliferation, and remodeling phases. Immediately after injury, hemostasis occurs and is characterized by vasoconstriction and blood clotting, which prevents blood loss and provides the provisional matrix for cell migration. Platelets secrete growth factors and cytokines attract fibroblasts, endothelial cells, and immune cells to initiate the healing process. The subsequent inflammation phase lasts up to 7 days. The predominant cells at work in this phase are phagocytic cells, such as neutrophils and macrophages. Neutrophils release reactive oxygen species (ROS) and proteases that prevent bacterial contamination and cleanse the wound of cellular debris. Blood monocytes arrive at the wound site and differentiate into tissue macrophages. The latter not only remove bacteria and nonviable tissue by phagocytosis, but also release various growth factors and cytokines recruiting fibroblasts, endothelial cells, and keratinocytes to repair the damaged blood vessels. As the inflammatory phase subsides accompanied by apoptosis of immune cells, the proliferation phase begins. This phase is primarily characterized by tissue granulation, formation of new blood vessels (angiogenesis), and epithelialization. The last phase occurs once the wound has closed and may last 1-2 years or longer. During this phase, the provisional matrix is remodeled into organized collagen bundles.

As used herein, in the present context, the term "chronic ulcer" refers to a heterogeneous group of ulcer types including, but not limited to diabetic ulcers, including diabetic foot ulcers as well as other diabetic ulcers, including chronic ulcers of the legs and hands, venous ulcers, including venous leg ulcers, arterial ulcers, decubitus (pressure) ulcers, varicose ulcers, and stasis ulcers. Chronic ulcers fail to proceed through the normal phases of healing in an orderly and timely manner. Commonly, a chronic ulcer is stalled in the inflammation phase. Commonly, chronic ulcers fail to achieve sufficient healing after 4 weeks.

The closure and regeneration of chronic skin ulcers is a different medical problem, involving different mechanisms than normal (acute) skin wounds for the multiple reasons discussed in the present disclosure. For example, in subjects having venous leg ulcers, venous hypertension, pressure, and infection can contribute to the stalled healing of the venous leg ulcer. Particularly, compared to a subject with a normally-healing wound, the subject may have increased pressure in the distal veins of the legs, excessive fibrin deposition around capillary beds, enlargement of endothelial pores, decreased oxygen permeability and tissue hypoxia, trapped growth factors and inflammatory cells in the fibrin cuff, release of proteolytic enzymes, release of reactive oxygen species (ROS), dysregulation of various pro-inflammatory cytokines, growth factors and MMPs. For example, in subjects having diabetic foot ulcers, polyneuropathy, vasculopathy, pressure, and infection can contribute to the stalled healing of the diabetic foot ulcer. Particularly, compared to a subject with a normally-healing wound, the subject may have increased formation of glycoproteins, basement membrane thickening, reduced endothelial proliferation, decreased vessel permeability, altered cell migration, high concentrations of inflammatory cytokines, cellular senescence, increased protease enzymes, degraded growth factors, receptors, matrix and support structures, decreased angiogenesis, and imbalance of MMPs and TIMPs.

Cellular and molecular data from numerous clinical studies suggest that most chronic ulcers get "stuck" in a prolonged inflammatory phase that is due to the presence of both planktonic (free flowing) and biofilm bacteria in the ulcers. The bacteria stimulate production of pro-inflammatory cytokines like tumor necrosis factor-$\alpha$ (TNF-$\alpha$) and interleukin 1 (IL-1), which act as chemotactic factors (chemical messengers} to recruit neutrophils, macrophages, and mast cells into the ulcers. The inflammatory cells that are drawn into the ulcers secrete proteases (MMPs, neutrophil elastase, and plasmin) and ROS in an attempt to kill bacteria and detach biofilm colonies that are tightly attached to the ulcer bed. However, because bacterial biofilms are tolerant to ROS as well as antibodies and even antiseptics, the biofilms persist and continue to stimulate inflammation. This results in chronically elevated levels of proteases and ROS that eventually begin to destroy essential proteins that are necessary for healing, including growth factors, their receptors, and ECM proteins. These "off-target" effects of proteases and ROS combine to reduce cell proliferation, migration. and generation functional scar matrix. The "biological sum" of this prolonged inflammatory state is a distorted molecular and cellular environment that prevents healing. In the simplest terms, the molecular and cellular environment between acute healing wounds and chronic ulcers is totally different.

Acute wounds, i.e., those that normally and orderly progress through the healing process, are characterized by relatively low inflammatory cytokines, low proteases, low ROS, intact functional matrix, high mitogenic activity, and mitotically competent cells. In contrast, chronic ulcers are characterized by one or more of relatively high inflammatory cytokines, relatively high proteases, relatively high ROS, degraded and non-functional matrix, low mitogenic activity, and senescent cells.

MMPs modify the ECM and modulate the chemical messages important in cell-to-cell communication. The MMP gene family contains a zinc2+binding domain in their active sites and calcium ions to interconnect folds and maintain structure. Enzymes are divided into subfamilies of secretory enzymes (collagenases, gelatinases, stromelysins, unclassified), and membrane-bound type enzymes (MT-MMPS) based upon structural characteristics and the substrates they preferentially bind. During normal healing, keratinocytes, fibroblasts, macrophages and endothelial cells secrete MMPs and express MT—MMPs on their surfaces. In chronic ulcers, excessive protease activity from elevated levels of collagenase and gelatinase interfere with proper granulation tissue formation. MMPs support healing, morphogenesis, tissue resorption and remodeling, nerve growth and hair follicle development. In chronic ulcers, the average level of protease activity was found to be approximately 116-fold higher than in acute wound fluids. Furthermore, as chronic venous ulcers began to heal, the levels of protease activity decreased. Similar results were reported for fluids or biopsies of chronic pressure ulcers, where levels of MMP-2, MMP-9, and MMP-4 were 10 to 25 times higher than levels in acute surgical wound fluids. Levels of the TIMPs, which are the natural inhibitors of MMPs, were found to be decreased in fluids from chronic venous ulcers compared to acute mastectomy wound fluids. In non-healing chronic pressure ulcers, MMP-8, the neutrophil-derived collagenase, was elevated, indicating that there may be persistent influx of neutrophils releasing MMP-8 and elastase, which could contribute to the destruction of ECM proteins and growth factors that are essential for healing. Chronic venous ulcers were found to have 10-fold to 40-fold higher levels of neutrophil elastase activity and to have degraded a 1-antitrypsin. Elevated MMP-2 and MMP-9 levels in chronic venous ulcers also were observed to coincide with degradation of fibronectin in the wound bed. Fibronectin is an important multi-domain adhesion protein that is present in the ECM and granulation tissue and is important in promoting epithelial cell migration. Proteases in chronic wound fluids were shown to rapidly degrade exogenously added growth factors, such as TGF-$\alpha$, epidermal growth factor (EGF), or platelet-derived growth factor (PDGF), using in-vitro laboratory tests. In contrast, exogenously added growth factors were stable when added to acute surgical wound fluids.

Bacterial burden of the ulcer refers to the biofilm, planktonic organisms, and toxins in the ulcer. Growth factors are degraded in the presence of significant quantities of bacteria in the ulcer. Protease activity arising from bacterial proteases and MMPs secreted in response to bacterial antigen or toxins inactivate local growth factors. The presence of fibroblasts enhances the degradation suggesting they may be the source of the MMPs production. All chronic ulcers have a bacterial load, usually consisting of normal flora. Although not an invasive infection, colonization may impede healing by creating a pro-inflammatory environment with secreted proteases decreasing available growth factor effect.

Bacterial virulence, pathogenicity, bacterial load, and toxins in association with host defense determine the extent of inhibition created by colonizing organisms. The term, critical colonization, describes the situation where there are no systemic signs of colonization, but healing fails to progress along the anticipated trajectory. In the presence of replicating organisms, the ulcer may exhibit excessive drainage, pain, odor, bright red fleshy friable granulation tissue, epithelial islands or epithelial bridging. For adequate wound healing to progress, bacterial balance must be established by decreasing organisms to a level easily managed by host defenses.

Bacterial biofilms are known to contribute to numerous chronic inflammatory diseases, and recent evidence suggests that biofilms also play an important role in impairing healing in chronic ulcers. Wound bacteria that grow in clumps embedded in a thick, self-made, protective, slimy barrier of sugars and proteins are called a wound biofilm. Biofilms are defined as complex, dynamic microbial communities made up of microorganisms (bacteria and fungi) that synthesize and secrete a protective matrix that attaches the biofilm firmly to the wound surface. They consist of a single bacterial or fungal species or, more commonly, may be poly-microbial, that is, they contain multiple diverse species that are continuously changing. A biofilm is a surrounded by an extracellular polymeric matrix (EPM), which attaches to a surface. Recent studies demonstrate that biofilms are becoming a significant component of infections in humans. Both acute and chronic ulcers are susceptible to the development of biofilms.

Open ulcers provide a perfect environment for opportunistic: organisms, such as bacteria, to reside and reproduce. Analyses of the microflora of chronic ulcers (such as pressure and diabetic foot ulcers) demonstrate a phenomenon known as chronic ulcer pathogenic biofilms. Typical mechanisms by which biofilms impede ulcer healing progress involve heightening the level of inflammation; increasing the amount of ROS and proteases in the wound bed; stimulating overly aggressive immune responses; producing detrimental exogenous toxins within the ulcer environment; and impairing normal chemokine signaling pathways. Aerobic organisms within biofilms use oxygen and help to create anaerobic niches within the biofilm matrix that support the development of anaerobes within the biofilm. Importantly, the presence of biofilms in an ulcer may affect the healing process without visible clinical signs of infection.

Biofilms trigger a chronic inflammatory response that results in the accumulation of neutrophils and macrophages surrounding biofilms. The neutrophils and macrophages secrete high levels of ROS that affect the biofilm and the surrounding tissue. Inflammatory cells also secrete high levels of proteases (MMPs and elastase) that can help to break down the attachments between biofilms and the tissue, dislodging the biofilms from the tissue. However, the ROS and proteases also damage normal surrounding tissue, proteins, immune cells, and tissue cells, impairing healing.

Closely linked to the bacterial bioburden in an ulcer is the pro-inflammatory cytokine profile. In general, fluids from acute healing wounds tend to have an early peak of major pro-inflammatory cytokines, TNT-$\alpha$ and IL-1$\beta$ and their natural inhibitors, P55 and IL-1 receptor antagonist, within the first few days after injury. This corresponds to the rapid increase in inflammatory cells in acute wounds. The levels of pro-inflammatory cytokines begin to decrease after 6 to 7 days as the inflammatory stimuli in acute wounds decrease. However, in a study of chronic leg ulcers, the levels of inflammatory cytokines, IL-1$\beta$, IL-6 and TNT-$\alpha$ were significantly higher than in acute healing wounds, and as the chronic ulcers began to heal, the levels decreased. These findings indicate that chronic ulcers have persistently elevated levels of pro-inflammatory cytokines, but in cases where chronic ulcers begin to heal, the molecular environment changes to a less inflammatory environment.

New blood vessel growth is a vital factor in the development of healthy granulation tissue. At least twenty angiogenic factors have been identified. Some promote blood vessel growth as their primary function like vascular endothelial growth factor (VEGF); while others, appear to promote neo-vascularization as an additional process. In addition to VEGF, angiogenic factors commonly encountered in the healing wound include fibroblastic growth factor acidic and basic (FGFa, FGFb), interleukin-8 (IL-8), platelet-derived growth factor BB (PDGF-BB), transforming growth factor-$\alpha$ (TGF-$\alpha$), transforming growth factor-$\beta$ (TGF-$\beta$), and tumor necrosis factor-$\alpha$ (TNF-$\alpha$). When angiogenic factors are produced in excess of inhibitors wound healing occurs. In pro-inflammatory states some angiogenic factors are produced in excess, which might account for the production of granulomatous tissue in infected wounds. However, when angiogenic factor production decreases in response to decreased production or inhibition granulation tissue does not develop. There are at least thirty angiogenic inhibitors. Angiogenic inhibitors-interferon (IFN-$\alpha$, $\beta$ and $\gamma$), fibronectin fragment, matrix metalloproteinase inhibitors (TIMPs), plasminogen activator inhibitor, retinoids, and thrombospondin-1 (TSN-1) balance wound angiogensis. Interestingly, TGF-$\beta$ exerts opposing effects both as an angiogenic stimulator and as an angiogenic inhibitor.

Cellular aging is a term used to describe the phenotypical changes that occur in cells that are slow to function secondary to oxidation of cellular components. Typically, these changes are seen in older cells that have encountered oxidative stress over time. The term has also been used to refer to cells that are obtained from older individuals and now function less aggressively because of the genetic changes that occur in older individuals secondary to life-time exposures to reactive oxygen species. More recently the term has been used to refer to senescent cells that function as though they were older cells or obtained from older individual. These macrophages, fibroblasts and keratinocytes found at the margin of wound beds respond sluggishly to stimulation with appropriate chemotactic agents or growth factors. Whether the oxidative stress occurs cumulative over decades as in elderly patients or gradually over weeks as with a chronic wound, cellular oxidation confers changes that preclude RNA and protein synthesis. The inability to aggressively respond to stressors with appropriately synthesized protein (enzymes) confers the phenotype of a non-functional or poorly functioning cell.

Characteristically, elderly skin thins, wrinkles, develops increased fragility, and becomes more susceptible to ulceration. Decreased dermal turnover, slowed toxin clearance, and inadequate skin immune dysfunction are also noted Inflammatory cells migrate more slowly into ulcer beds and a generalized decline in cellular function is observed in aged skin of the elderly. On the other hand, cells residing in the base and margin of ulcer beds fail to properly migrate, secrete, and divide when given the usual level and type of stimuli. It is unclear if the failure is related to an inability to acquire the message at the level of the cell receptor, a malfunction in the transmission of the information within the cell, or a direct blockage at the level of RNA and protein synthesis. Alternatively, the abnormality may arise from chemical inhibitors present at the receptors or within the cell.

Another key concept that emerged from laboratory analysis demonstrates that the mitogenic activity of chronic ulcer fluids is dramatically less than levels in acute wound fluids. Furthermore, when acute wounds and chronic ulcer fluids were combined, the mitotic activity of acute wound fluids was inhibited. These results show that the proteases in chronic ulcer fluids degrade growth factors that are normally present in acute wound fluids and without the essential actions of these growth factors, healing will not progress. In chronic ulcers, the capacity of the wound cells to respond to cytokines and growth factors is altered. Research suggests that fibroblasts (cells that manufacture collagen and perform other essential functions in wound healing) have a diminished response to growth factors in chronic ulcers. For example, fibroblast cultures established from chronic venous leg ulcers proliferated slowly and formed less dense confluent cultures when compared to normal fibroblast cultures established from uninjured dermis. In another study of chronic venous leg ulcers that were present for more than 3 years, fibroblasts proliferated poorly in response to PDGF added to cell-culture medium and rapidly approached senescence compared to fibroblasts cultured from venous ulcers that had been present for less than 3 years.

As used herein, in the present context, the term "surgical wound" refers to a heterogeneous group of wound types including, but not limited to wounds at surgical sites including donor sites, graft sites, Mohs surgery sites, laser surgery sites, podiatric surgical sites, post-surgical sites, and dehiscence.

In certain aspects, the present disclosure includes a multilayer sheet of collagen material for use in accordance with methods of the present disclosure. As used herein, the term "pliable" means that the material conforms and adheres naturally to the chronic ulcer site upon hydration.

The multilayer sheet of collagen material comprises (i) a barrier layer of collagen material having a smooth face and a rough fibrous face opposite said smooth face and (ii) a spongeous matrix layer of collagen material connected to said rough fibrous face, said spongeous matrix layer having an open sponge-like texture. In some aspects, the multilayer sheet of collagen material may include i) peritoneal porcine collagen membranes that are purified and treated such that they contain native (not denatured), insoluble collagen in its natural collagen structure; and ii) collagen fibers that are purified and treated such that they have an open fibrous structure. The multilayer sheet of collagen material is acellular, virally-inactivated, and has a three-dimensional multilayer structure, wherein the layers are not laminated. As used herein, the term "lower layer" refers to the spongeous layer of the multilayer sheet of collagen material that faces the chronic ulcer and the "upper layer" is the layer of the multilayer sheet of collagen material facing away from the chronic ulcer. The upper layer protects the ulcer and the open healing process. The upper layer has a smooth texture with appropriate pull out strength properties to allow suturing. The lower layer is a porous spongeous collagen scaffold that is highly biocompatible. In certain aspects, the matrix structure includes interconnected pores about 0.001 to 1000 μm in diameter, e.g., 10 to 400 μm, 20 to 200 μm, 30 to 180 μm, 40 to 150 μm, or any other diameter in the disclosed range. In certain aspects, the porosity is about 80 to about 98% void volume, e.g., 82 to 96%, 84 to 94%, 86 to 92%, 88% to 90%, or any other percentage in the disclosed range. In certain aspects, the thickness ratio between the lower layer and the upper layer is about 10:1 to 2:1, about 8:1 to 3:1, or about 6:1 to 4:1. In certain aspects, the multilayer sheet of collagen material has a liquid uptake capacity such that the weight of the wet multilayer sheet of collagen material is about 6 to about 15 times, or about 7 to about 12 times, or about 8 to about 10 times the weight of the multilayer sheet of collagen material in dry state, including uptake of blood. The multilayer sheet of collagen material includes sterile collagen Type I. In certain aspects, the multilayer sheet of collagen material comprises greater than 60%, greater than 80% or greater than 85% collagen Type I. In certain aspects, the multilayer sheet of collagen material has been sterilized by γ irradiation or X-ray irradiation. The multilayer sheet of collagen material has low antigenicity and low immunogenicity.

The multilayer sheet of collagen material has properties such that it can easily be manipulated, cut and shaped in the surgical theater or in private practice. In some aspects, the multilayer sheet of collagen material has not been artificially cross-linked or chemically treated, and has a thickness of ranging from about 0.5 mm to about 25 mm, about 0.5 to about 10 mm, about 1 mm to about 8 mm, about 2 mm to about 6 mm, about 2.5 mm to about 5 mm, about 3 mm, about 4 mm, or about 5 mm, or any thickness encompassed by any of the preceding ranges. In some aspects, the multilayer sheet of collagen material is circular with a diameter ranging from about 5 mm to about 40 mm, about 10 mm to about 30 mm, about 12 mm to about 26 mm, about 12 mm, about 14 mm, about 16 mm, about 18 mm, or about 20 mm, or any diameter encompassed by any of the preceding ranges. In some aspects, the multilayer sheet of collagen material is rectangular (including square-shaped) with side lengths ranging from about 5 mm to about 100 mm, about 10 mm to about 80 mm, about 15 mm to about 60 mm, about 20 mm to about 50 mm, about 25 mm to about 40 mm, about 30 mm to about 35 mm, about 15 mm, about 20 mm, about 25 mm, about 30 mm, about 40 mm or about 50 mm, or any length encompassed by any of the preceding ranges.

In certain aspects, the multilayer sheet of collagen material of the present disclosure comprises, consists essentially of, or consists of treated porcine peritoneal membranes and treated porcine hides produced having the basic and novel structure and properties according to the present disclosure. As used herein, the phrase "consisting essentially of" in the context of the multilayer sheet of collagen material means that the material has not been modified by additional artificial cross-linking, has not had any growth factors or other wound- or ulcer-treating agents added to it, has not had any antimicrobial agents added to it, and/or has not undergone any modification, treatment or adulteration to materially affect the basic and novel characteristics of the multilayer sheet of collagen material of the present disclosure.

In certain aspects, the present disclosure includes a method of preparing a multilayer sheet of collagen material for use in accordance with methods of the present disclosure. In certain aspects, a multilayer sheet of collagen material can be prepared in accordance with methods disclosed in U.S. Pat. No. 6,713,085 (Geistlich, Schloesser, and Boyne) and U.S. Pat. No. 5,837,278 (Geistlich, Eckmayer and Boyne), the disclosures of which are incorporated herein by reference in their entireties. In certain aspects, the method of preparing a multilayer sheet of collagen material for use in accordance with methods of the present disclosure involves producing materials (A) and (B) and combining the products to form the multilayer sheet of collagen material in accordance with the present disclosure.

Method of Producing Material (A). In certain aspects, the method of producing material (A) includes mechanically freeing porcine peritoneal membranes from flesh and grease to form porcine peritoneal membrane material that is free of flesh and grease, washing the freed porcine peritoneal membrane material with water to form a washed and freed porcine peritoneal membrane material, treating the washed and freed porcine peritoneal membrane material with a base (e,g., NaOH at a concentration of about 0.5 to about 10%, about 1 to about 6%, about 2 to about 4%, or about 2%) for about 6 to about 20 hours, about 8 to about 16 hours, about 10 to about 14 hours, or about 12 hours, to form base-treated washed and freed porcine peritoneal membrane material, washing the base-treated washed and freed porcine peritoneal membrane material with water, and acidifying through its entire thickness the resulting base-treated washed and freed porcine peritoneal membrane material with an acid solution, e.g, HCl, at a concentration of about 0.1 to about 1%, about 0.2 to about 0.7%, about 0.3 to about 0.5%, or about 0.32%, to form an acidified porcine peritoneal membrane material. After acidifying through its entire thickness, the method includes washing the acidified porcine peritoneal membrane material until a pH of about 2 to about 5, about 3 to about 4, or about 3.5 is reached. In certain aspects, after washing the acidified porcine peritoneal membrane material, the method includes shrinking the washed acidified porcine peritoneal membrane material with saline solution at a concentration of about 4 to about 12%, about 5 to about 10%, about 6% to about 8%, or about 7% saline. In certain aspects, the method includes neutralizing the shrunk porcine peritoneal membrane material with a neutralizing agent, e.g., $NaHCO_3$ solution at a concentration of about 0.1 to about 5%, about 0.5 to about 3%, or about 1% $NaHCO_3$ to form a neutralized and shrunk porcine peritoneal membrane material. In certain aspects, the method includes washing the neutralized and shrunk porcine peritoneal membrane material with water. In certain aspects, the method includes dehydrating the neutralized and shrunk porcine peritoneal membrane material to form a dehydrated porcine peritoneal membrane material. In certain aspects, the dehydrating step is performed using acetone. In certain aspects, the method includes further degreasing the dehydrated porcine peritoneal membrane material. In certain aspects, the further degreasing step is performed using n-hexane. In certain aspects, the method includes drying the degreased dehydrated porcine peritoneal membrane material to form a dried porcine peritoneal membrane material. In certain aspects, the drying step is performed using ethanol ether.

Method of Producing Material (B). In certain aspects, the method of producing material (B) includes grinding porcine hides to form 1 to 20 mm pieces of ground porcine hide, removing water from the ground porcine hides to form collagen fibers, defatting the collagen fibers using a solvent, removing the solvent to form solvent-treated defatted collagen fibers, treating the solvent-treated defatted collagen fibers with a strong inorganic base at a pH of above 12 for about 6 to about 24 hours to form base-treated collagen fibers, treating the base-treated collagen fibers with a strong inorganic acid at a pH of about 0 to about 1 for about 1 to about 12 hours to form acid-treated collagen fibers, removing acid by rinsing with water to form rinsed acid-treated collagen fibers, homogenizing the rinsed acid-treated collagen fibers in the present of a swelling regulator to form homogenized collagen fibers, drying the homogenized collagen fibers to form dried collagen fibers, cleaning the dried collagen fibers using one or more organic solvents, evaporating the solvents under vacuum to a solvent residue of less than 1% to form cleaned, dried collagen fibers, and mixing the cleaned, dried collagen fibers with water to form a collagen fiber slurry. In certain aspects, the water-soluble solvent is an alcohol or a ketone. In certain aspects, the defatting step is performed using a chlorinated hydrocarbon or a non-chlorinated hydrocarbon. In certain aspects, the chlorinated hydrocarbon is dichloroethane, methylene chloride, or a combination thereof. In certain aspects, the non-chlorinated hydrocarbon is hexane, toluene, or a combination thereof. In certain aspects, the swelling regulator is an inorganic salt. In certain aspects, the homogenized collagen fibers are dried by freeze-drying. In certain aspects, the one or more organic solvents are alcohols, ethers, ketones, chlorinated hydrocarbons, or combinations thereof.

In certain aspects, a method of preparing a multilayer sheet of collagen material of the present disclosure includes pouring the collagen fiber slurry of material (B) onto the dried porcine peritoneal membrane material (A) to form a combination product, or alternatively pouring the slurry of collagen material (B) into a recipient and laying the fibrous face of membrane (A) on top of the slurry of collagen material, the w/w ratio of slurry of collagen material (B) to the membrane (A) in dry state being generally from 25/1 to 1/5, usually from 15/1 to 1/2, allowing (A) and (B) to combine, and freeze-drying the combined product. In certain aspects, the method includes allowing (A) and (B) to combine for about 10 to about 60 minutes, about 20 to about 40 minutes, or about 30 minutes before freeze-drying.

The present disclosure provides a method for implanting the multilayer sheet of collagen material into a chronic ulcer. In some aspects, the method includes cleaning the chronic ulcer site to remove bacteria and other pathogens as well as debridement so that it is free of debris and devitalized tissue prior to and/or during implantation of the multilayer sheet of collagen material. In some aspects, the chronic ulcer is debrided. In some aspects, the chronic ulcer site is debrided until the edges of the ulcer contain viable tissue. In some aspects, the chronic ulcer site is debrided with a surgical sharp spoon or scalpel prior to and/or during implantation of the multilayer sheet of collagen material. In some aspects, the chronic ulcer site is debrided with gauze prior to and/or during implantation of the multilayer sheet of collagen material. In some aspects, the method includes removing exudate from the chronic ulcer site prior to and/or during implantation of the multilayer sheet of collagen material. In some aspects, the method includes reducing or inhibiting bleeding at the chronic ulcer site prior to and/or during implantation of the multilayer sheet of collagen material. In some aspects, alcohol-containing disinfectant is not used at the chronic ulcer site prior to, during or after implantation of the multilayer sheet of collagen material. In some aspects, iodine-containing disinfectant is not used at the chronic ulcer site prior to, during or after implantation of the multilayer sheet of collagen material.

In some aspects, the method includes providing the multilayer sheet of collagen material in a sterile blister. In some aspects the blister is provided in a pouch. In some aspects, the method includes aseptically trimming the multilayer sheet of collagen material to the desired size and/or shape to form an implant for the chronic ulcer. In some aspects, the method includes using a scalpel, shears, scissors, and/or graspers to trim and/or shape the multilayer sheet of collagen material to form an implant. In some aspects, the method includes applying the multilayer sheet of collagen material to the chronic ulcer site with the lower layer facing the chronic ulcer. In some aspects, the method includes directly applying the multilayer sheet of collagen material to the chronic ulcer site in a dry state. As used herein, "a dry state" means that no soaking or rinsing is performed prior to application. In some aspects, the method includes storing the multilayer sheet of collagen material at a temperature of between about 10 to about 30° C., about 12 to about 27° C., or about 15 to about 25° C. prior to the implanting step.

In some aspects, the method includes fixing the multilayer sheet of collagen material in the chronic ulcer site. In some aspects, the method includes applying an adhesive, e.g., a surgical or organic adhesive. In some aspects, no adhesive is used. In some aspects, the method includes suturing and in other aspects, the method does not involve suturing the multilayer sheet of collagen material. In some aspects, the method includes implanting the multilayer sheet of collagen material in the chronic ulcer and then completely hydrating the multilayer sheet of collagen material in situ. In some aspects, the hydrating is performed using blood, sterile saline solution, or a combination thereof. In some aspects, the method includes applying a first dressing that covers the chronic ulcer site having the multilayer sheet of collagen material implanted therein. In some aspects, the method includes providing a hydrocolloid dressing over the chronic ulcer site having the multilayer sheet of collagen material implanted therein.

In some aspects, the method includes applying a secondary dressing or re-dressing the chronic ulcer site, e.g., a composite dressing, a gauze dressing, or a film dressing. In some aspects, the secondary dressing or re-dressing is non-adhesive. In some aspects, the method includes applying sterile saline to remove a dressing material from the multilayer sheet of collagen material. In certain aspects, the method includes periodically (e.g. every day, second day, third day, fourth day or every week) changing the dressing over the implanted multilayer sheet of collagen material until wound closure. The period for wound closure is generally from 1 to 12 weeks after implantation, usually from 1 to 6 weeks after implantation and often from 1 to 4 weeks after implantation. In certain aspects, the method includes changing the secondary dressing over the first dressing every day, second day, every fourth day or every week after implantation. In certain aspects, the method includes removing exudate from the chronic ulcer site every day, second day, third day, fourth day or every week after implantation. In certain aspects, the method includes not using a dressing. In certain aspects, the method includes not using a dressing after a first visible epithelialization is observed. In certain aspects, the method includes continuing the monitoring and/or re-dressing steps for 3 to 24 weeks, 4 to 12 weeks, or 5 to 10 weeks after implantation.

In certain aspects, the method includes monitoring the size, shape, color, inflammation, and drainage of the edges of the chronic ulcer site every day, second day, third day, fourth day or every week after implantation. In certain aspects, the method includes removing the implanted multilayer sheet of collagen material and repeating the implanting step. In certain aspects, if the monitoring step reveals redness, swelling, hematomas, blistering, inflammation, excess exudate, infection, and/or necrosis at the chronic ulcer site, the method includes removing the implanted multilayer sheet of collagen material and repeating the method steps of the present disclosure.

In certain aspects, the method includes ensuring that the chronic ulcer site is free of necrotic tissue or acute infection before implanting the multilayer sheet of collagen material. In certain aspects, the method includes treating infections at or near the chronic ulcer site prior to implanting the multilayer sheet of collagen material using known anti-infective therapies, e.g., antibiotics. In certain aspects, the method includes not using antimicrobials in combination with the implant. In certain aspects, the method includes identifying patients with allergies or sensitivities to porcine or collagen materials prior to implanting the multilayer sheet of collagen material.

In certain aspects, the chronic ulcer area is from about 1 $cm^2$ to about 150 $cm^2$, about 3 $cm^2$ to about 100 $cm^2$, about 4 $cm^2$ to about 50 $cm^2$, or about 6 $cm^2$ to about 12 $cm^2$, or any area encompassed by any of the preceding ranges. Typically, the chronic ulcer area is from 1 to 20 $cm^2$. In some aspects, the present disclosure includes a method for implanting multiple pieces of the multilayer sheet of collagen material of the present disclosure into a chronic ulcer, e.g., pieces having different sizes and/or shapes.

In certain aspects, the present disclosure includes a method step of inspecting, monitoring, observing, diagnosing, and/or ensuring that malignant degeneration and neoplastic lesions are not present at the chronic ulcer site. In certain aspects, the present disclosure includes classifying the chronic ulcer. For diabetic foot ulcers, the Wagner, University of Texas, and PEDIS classification systems may be used. For venous leg ulcers, the Clinical-Etiology-Anatomy-Pathophysiology (CEAP) classification system may be used. For pressure ulcers, the National Pressure Ulcer Advisory Panel (NPUAP) classification schemes may be used.

In certain aspects, the present disclosure provides a method for reducing formation of glycoproteins in a chronic ulcer, reducing basement membrane thickening in a chronic ulcer, increasing vessel permeability in a chronic ulcer, reducing concentration of inflammatory cytokines in a chronic ulcer, reducing cellular senescence in a chronic ulcer, decreasing protease enzymes in a chronic ulcer, inhibiting degradation of growth factors in a chronic ulcer, inhibiting degradation of receptors in a chronic ulcer, inhibiting degradation of matrix structures in a chronic ulcer, increasing angiogenesis in a chronic ulcer, and/or rebalancing MMPs and TIMPs in a chronic ulcer.

In certain aspects, the present disclosure includes obtaining ankle-brachial indices (ABI) at baseline for patients. When the ABI is below 0.9, the patient should be classified as having impaired arterial perfusion. In certain aspects, the present disclosure includes performing one or more of toe-blood pressure readings, pulse volume recordings, transcutaneous oxygen measurements, and skin perfusion pressure measurements.

In certain aspects, the present disclosure includes using the multilayer sheet of collagen material of the present disclosure for promoting neutrophils and monocytes to localize at the chronic ulcer site, promoting formation of a multi-layered cell structure in the ulcer site, promoting conversion of monocytes to macrophages, promoting secretion of the patient's own growth factors, promoting tissue proliferation and cell migration, promoting production and cross-linking of collagen at the chronic ulcer site, promoting growth of endothelial cells, promoting angiogenesis that was stalled at the chronic ulcer site, promoting formation of a vascular network and granulation, promoting oxygenation of the chronic ulcer site, and reducing one or more of purulent drainage, erythema, pain, warming, tenderness, induration, and bleeding at the chronic ulcer site.

In certain aspects, the present disclosure includes implanting a multilayer sheet of collagen material that is free of or essentially free of one or more of glycosaminoglycan, chondroitin, silicone, cells, growth factors, hydrocolloids, hydrogels, alginate-containing compounds, iodine-containing agents, silver-containing agents, hydrogels, antimicrobial agents, cellulose-containing compounds, gel-forming materials, extracellular matrix components, equine-derived collagen, bovine-derived collagen, ovine-derived collagen, humectants, denatured collagen, gelatinous collagen, chelating agents (e.g., ethylenediaminetetraacetic acid (EDTA)), glutaraldehyde, amniotic membrane, chorion membrane, glucosamine, chitin, cotton, polysaccharide, pectin, cross-linking agents, proteases, human skin, latex, human-derived material, alcohol, cultured skin materials, mesh, foam, fibers, platelet-derived growth factor, nitric oxide, and intestinal submucosa-derived collagen. As used herein, "essentially free" means that the subject compound has not been added to the multilayer sheet of collagen material and any amount of the subject compound that is in the multilayer sheet of collagen material is present in trace amounts as a contaminant.

In certain aspects, the present disclosure includes a kit including one or more of a blister, a pouch, a multilayer sheet of collagen material of the present disclosure, instructions for use of the multilayer sheet of collagen material of the present disclosure, wherein the instructions for use require a user to take specific actions including one or more of the following: aseptically trimming the multilayer sheet of collagen material to the desired size and/or shape to form an implant; using a scalpel, shears, scissors, and/or graspers to trim and/or shape the multilayer sheet of collagen material to form an implant; applying the multilayer sheet of collagen material to the chronic ulcer site with the lower layer facing the chronic ulcer; directly applying the multilayer sheet of collagen material to the chronic ulcer site in a dry state; storing the multilayer sheet of collagen material at a temperature between generally about 10 to about 30° C., usually about 12 to about 27° C., or preferably about 15 to about 25° C. prior to the implanting step; applying an adhesive, e.g., a surgical or organic adhesive; not applying an adhesive; implanting the multilayer sheet of collagen material in the chronic ulcer and then completely hydrating the multilayer sheet of collagen material in situ using blood, sterile saline solution, or a combination thereof to hydrate the multilayer sheet of collagen material; applying a first dressing that covers the chronic ulcer site having the multilayer sheet of collagen material implanted therein; providing a hydrocolloid dressing over the chronic ulcer site having the multilayer sheet of collagen material implanted therein; applying a secondary dressing or re-dressing the chronic ulcer site; applying a non-adhesive secondary dressing or re-dressing; applying sterile saline to remove a dressing material from the multilayer sheet of collagen material; changing the dressing over the implanted multilayer sheet of collagen every 1 to 7 days after implantation; changing the secondary dressing over the first dressing every 1 to 7 days after implantation; removing exudate from the chronic ulcer site every day, second day, third day, fourth day or every week after implantation; monitoring the size, shape, color, inflammation, and drainage of the edges of the chronic ulcer site every 1 to 7 days after implantation; removing the implanted multilayer sheet of collagen material and repeating the implanting step; ensuring that the chronic ulcer site is free of debris and devitalized tissue as well as bacteria and other pathogens before implanting the multilayer sheet of collagen material; treating infections at or near the chronic ulcer site prior to implanting the multilayer sheet of collagen material; identifying patients with allergies or sensitivities to porcine or collagen materials prior to implanting the multilayer sheet of collagen material; and not implanting the multilayer sheet of collagen material in patients that have allergies or sensitivities to porcine or collagen materials.

As shown in FIG. 1, the chronic ulcer site may include an ulceration of the hypodermis, dermis and epidermis layers of the subject's skin. As discussed above, a chronic ulcer is stalled in the healing process and often involves chronic inflammation, an imbalance of growth factors and proteases, as well as reduced proliferation and migration of cells. The multilayer sheet of collagen material is implanted into the chronic ulcer site according to the method of the present disclosure and inactivates matrix metalloproteinases (MMPs) and binds the patient's own growth factors. The multilayer sheet of collagen material promotes cell migration and proliferation in the chronic ulcer site, and promotes angiogenesis and re-epithelialization.

Figure 2:
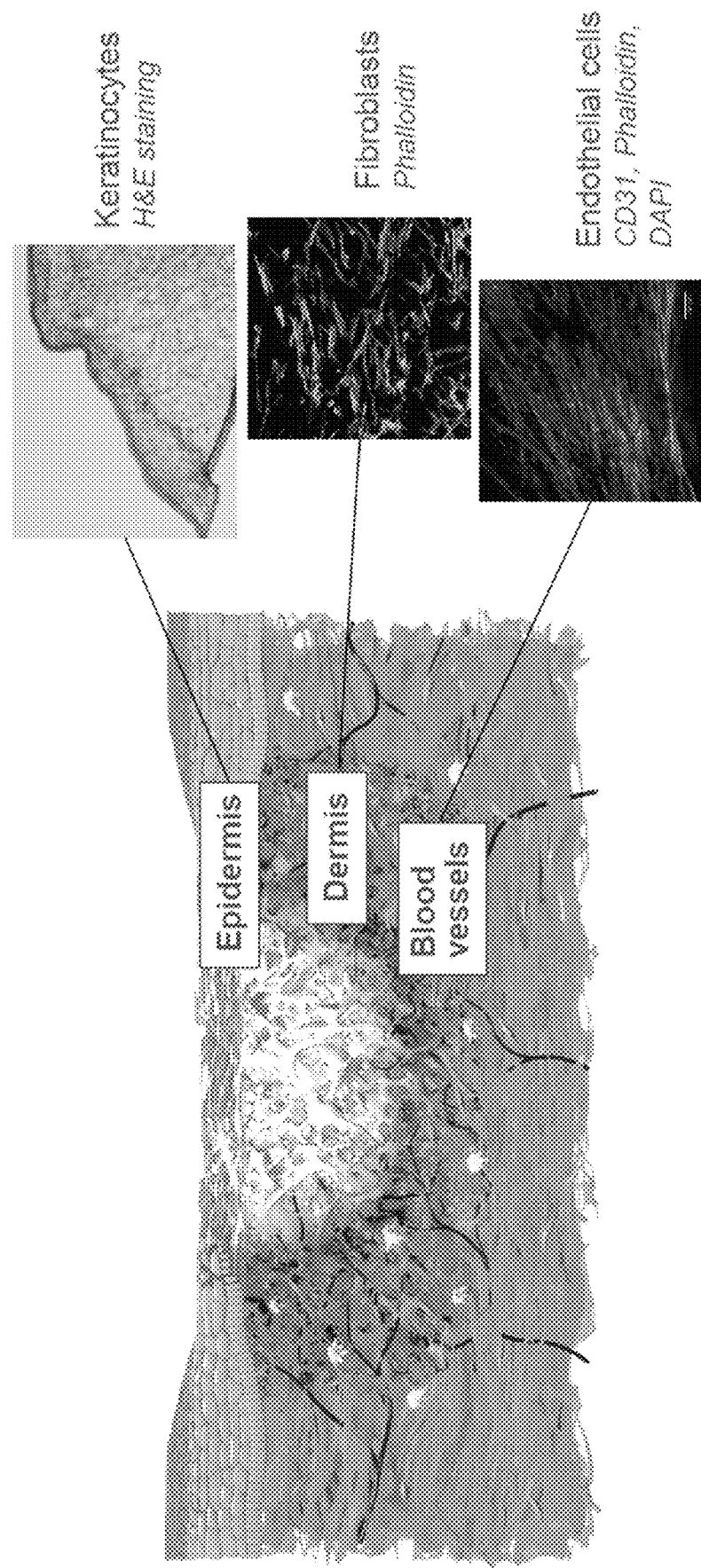
FIG. 2 is a schematic view of a multilayer sheet of collagen material according to one aspect of the present disclosure after days of implantation in a chronic ulcer site, with microscopy images of cells involved in the healing process (keratinocytes, fibroblasts and endothelial cells)

As shown in FIG. 2, the present disclosure provides a method of attracting fibroblasts, keratinocytes, endothelial cells, and blood vessels to the chronic ulcer site. The present disclosure provides a method of binding and preserving the patient's own growth factors at the chronic ulcer site, while inhibiting activity of MMPs (e.g., MMP1, MMP2, MMP-3, MMP-8, and MMP9) and other collagenases at the chronic ulcer site, and inhibits degradation of growth factors and the collagen matrix. In some aspects, the present disclosure provides a method of binding and preserving the patient's own growth factors at the chronic ulcer site, e.g., including but not limited to transforming growth factors (e.g., TGF-β), basic fibroblast growth factor (bFGF, also known as FGF2), epidermal growth factor (EGF), Insulin-like Growth Factor (IGF-1), Platelet-derived Growth Factor (PDGF), vascular endothelial growth factor (VEGF), and other bioactive growth factors in the chronic ulcer site.

Figure 3:
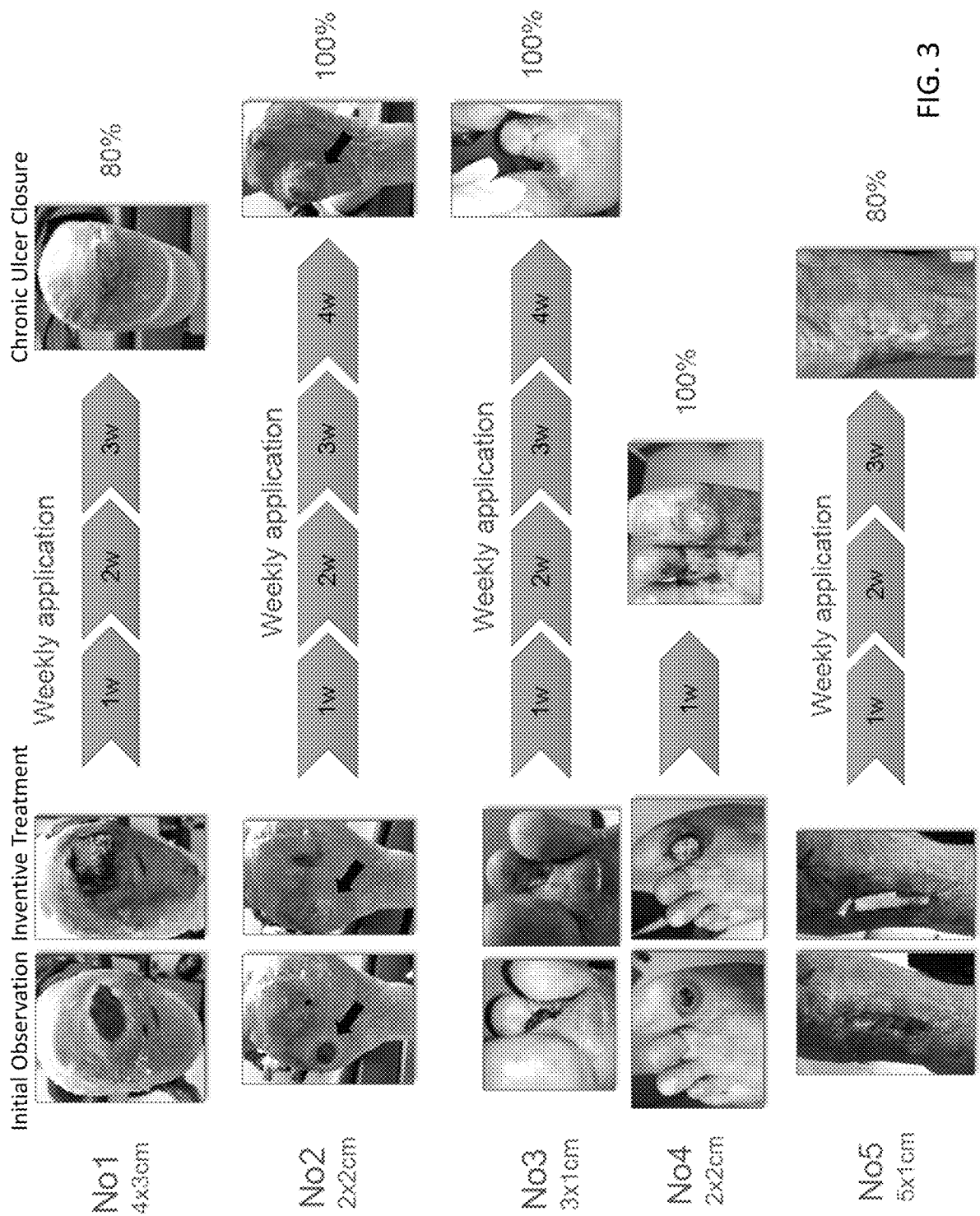
FIG. 3 contains photographs of DFU chronic ulcers for five different patients before and after treatment during different treatment periods (one week for patient No. 4, three weeks for patients Nos. 1 and 5 and four weeks for patients Nos. 2 and 3) according to one aspect of the present disclosure. The % given are the % of ulcer closure after the different treatment periods (ratio of the ulcer surface after treatment to the ulcer surface before treatment).
Figure 4:
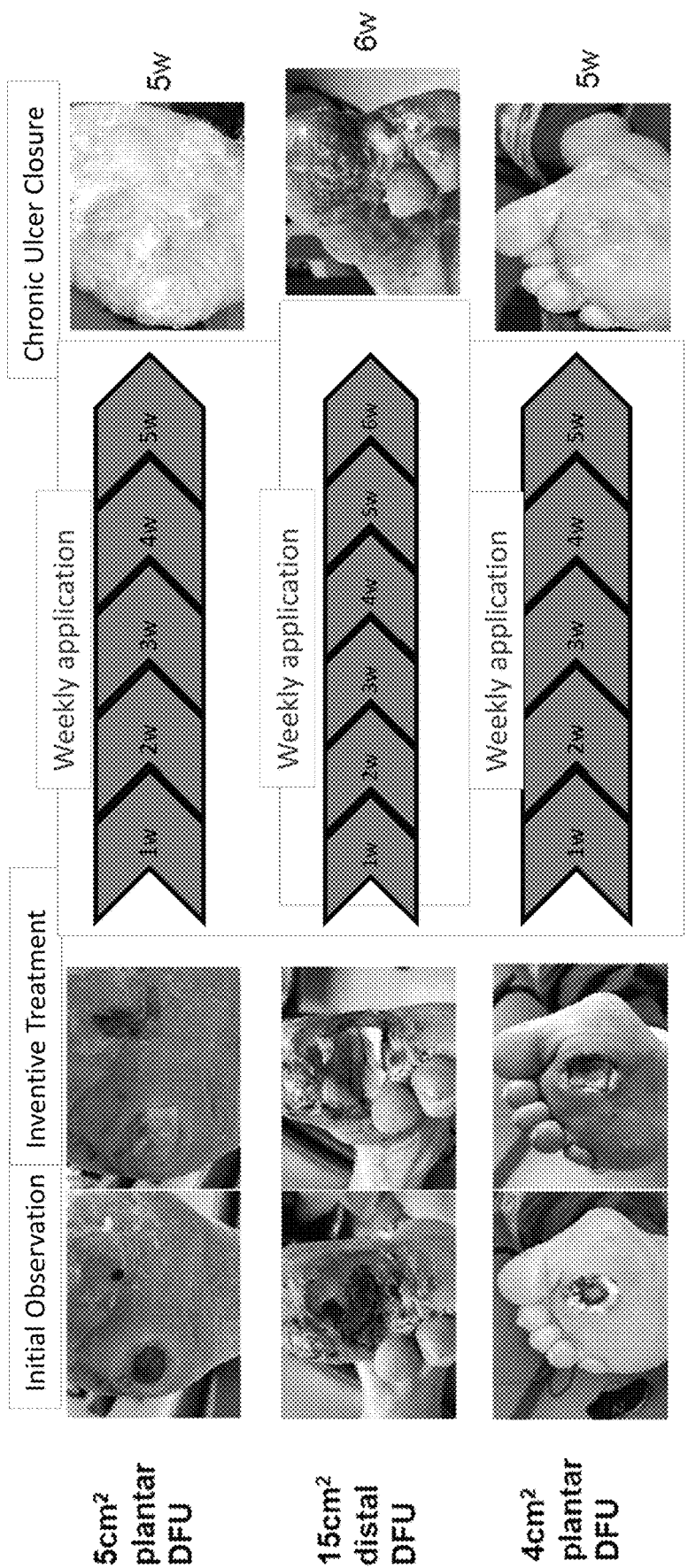
FIG. 4 contains photographs of DFU chronic ulcers for three different patients before and after treatment during different periods until 100% ulcer closure (five weeks for two patients and six weeks for one patient) according to one aspect of the present disclosure.

As shown in FIG. 3 and FIG. 4, the present disclosure unexpectedly provides a method of successfully closing chronic ulcers including in patients suffering from diabetic foot ulcers DFU. As shown in FIG. 3 and FIG. 4, the present disclosure unexpectedly provides a method of successfully closing chronic ulcers such as DFU within 1 week to about 6 weeks of the treatment of the present disclosure. In some aspects, the present disclosure provides a method of decreasing the chronic ulcer area by about 70% to about 100% within 1 week to about 6 weeks of the treatment of the present disclosure, with an average of about 2 to about 3 weeks for diabetic foot ulcers. As shown in FIG. 3, in one aspect, the present disclosure provides a method of decreasing the chronic ulcer area from 12 $cm^2$ to about 2 $cm^2$ within 3 weeks of the treatment of the present disclosure. As shown in FIG. 3, in one aspect, the present disclosure provides a method of decreasing the chronic ulcer area from 4 $cm^2$ to fully closed within 4 weeks of the treatment of the present disclosure. As shown in FIG. 3, in one aspect, the present disclosure provides a method of decreasing the chronic ulcer area of a diabetic foot ulcer from 3 $cm^2$ to fully closed within 4 weeks of the treatment of the present disclosure. As shown in FIG. 3, in one aspect, the present disclosure provides a method of decreasing the chronic ulcer area of a diabetic foot ulcer from 4 $cm^2$ to fully closed within 1 week of the treatment of the present disclosure. As shown in FIG. 3, in one aspect, the present disclosure provides a method of decreasing the chronic ulcer area of a diabetic foot ulcer from 5 cm² to about 1 cm² within 3 weeks of the treatment of the present disclosure.

As shown in FIG. 4, in one aspect, the present disclosure provides a method of decreasing the chronic ulcer area of a plantar foot ulcer from 5 cm² to fully closed within 5 weeks of the treatment of the present disclosure. As shown in FIG. 4, in one aspect, the present disclosure provides a method of decreasing the chronic ulcer area of a distal foot ulcer from 15 cm² to fully closed within 6 weeks of the treatment of the present disclosure. As shown in FIG. 4, in one aspect, the present disclosure provides a method of decreasing the chronic ulcer area of a plantar foot ulcer from 4 cm² to fully closed within 5 weeks of the treatment of the present disclosure.

The method of the present disclosure may reduce basement membrane thickening in diabetic foot ulcers, may increase vessel permeability in diabetic foot ulcers, may reduce concentration of inflammatory cytokines in diabetic foot ulcers, may reduce cellular senescence in diabetic foot ulcers, may decrease protease enzymes in diabetic foot ulcers, may inhibit degradation of growth factors in diabetic foot ulcers, may inhibit degradation of receptors in diabetic foot ulcers, may inhibit degradation of matrix structures in diabetic foot ulcers, may increase angiogenesis in diabetic foot ulcers, and/or rebalance MMPs and TIMPs in diabetic foot ulcers.

The present disclosure includes methods for promoting cellular attachment and proliferation. The method involves promoting fibroblast, keratinocyte, endothelial, and pluripotent stem cell attachment and proliferation within the material of the present disclosure in a chronic ulcer. As evident in comparison to full thickness skin, the upper layer mimics the basement membrane, supporting the attachment and growth of keratinocytes and suggesting an enhanced re-epithelialization. The lower layer beneath the compact layer accommodates fibroblasts and endothelial cells from the surrounding tissue, which may support healing through the production of ECM molecules and provision of nutrients to the epithelial layer. In some aspects, the present method involves a reassembling process without deleterious chemical crosslinking. The present disclosure advantageously provides a suitable ECM that supports cell attachment, migration, proliferation, differentiation and angiogenesis in the chronic ulcer.

In some aspects, the present disclosure includes methods for targeting multiple proteases in the proteolytic cascade and effectively modulating MMP activity over time particularly in the hyper-proteolytic environment of chronic ulcers. In some aspects, the present disclosure includes binding growth factors and preserving their bioactivity over the course of at least 72 hours in a chronic ulcer sit. In some aspects, the present disclosure includes retaining and protecting endogenous growth factors in the chronic ulcer and restarting arrested healing to proceed.

In some aspects, the present disclosure includes a method for providing a suitable pH environment in the chronic ulcer site. Pathogenic bacteria in the wound bed can contribute to creating an unsuitable healing environment. By providing a slightly acidic pH, growth of pathogenic bacteria and excessive breakdown extracellular matrix may be inhibited or prevented by the method of the present disclosure, and tissue oxygenation may be increased.

For a chronic ulcer such as a venous leg ulcer (VLU) or a diabetic foot ulcer (DFU), the method of the present disclosure may inhibit deposition of excess fibrin around capillary beds in the chronic ulcer, inhibit enlargement of endothelial pores in the chronic ulcer, increase oxygen permeability to tissue in the chronic ulcer, inhibit trapping of growth factors in the fibrin cuff of the chronic ulcer, inhibit trapping of inflammatory cells in the fibrin cuff of the chronic ulcer, inhibit release of reactive oxygen species in the chronic ulcer, and inhibit dysregulation of pro-inflammatory cytokines, growth factors and MMPs in the chronic ulcer.

Advantages of the present disclosure include avoiding the need to harvest tissue from the patient, avoiding high costs of currently available graft materials, which are often difficult to handle for surgeons and are made from human tissue. In addition, the present disclosure has the added advantages of not requiring fenestration and not requiring pre-treatment of the multilayer sheet of collagen material, e.g., no rinsing or pre-hydrating before implantation, thereby reducing implantation/surgical times, reducing risks of contamination and infection, and increasing ease of use. Further advantages include eliminating harvest-site pain and complications, shortening surgical times, and promoting natural tissue coloring, sheen, and structuring.

As used herein, the term "about" when used in connection with a numerical value should be interpreted to include any values which are within 5% of the recited value. Furthermore, recitation of the term about and approximately with respect to a range of values should be interpreted to include both the upper and lower end of the recited range.

The following items are included as part of the present disclosure:

1. A method of treating a chronic ulcer in a subject in need thereof, comprising:
   i) cleaning to remove bacteria and other pathogens and/or debriding the chronic ulcer until the edges of the ulcer contain viable tissue;
   ii) aseptically implanting into the chronic ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that the rough fibrous face of said barrier layer of collagen material to which is connected said spongeous matrix layer of collagen material having an open sponge-like texture, faces toward and is adjacent to the bed of the chronic skin ulcer;
   iii) hydrating the implanted multilayer sheet of collagen material in dry state; and
   iv) providing a dressing over the implanted, hydrated multilayer sheet of collagen material, thereby restarting stalled cell migration, proliferation and angiogenesis at the chronic ulcer site.
2. The method of item 1, wherein the collagen of said barrier layer of collagen material is predominantly collagen I, collagen III or a mixture thereof.
3. The method of item 1, wherein said the collagen of said spongeous matrix layer of collagen material is predominantly collagen I, collagen III or a mixture thereof.
4. The method of item 1, wherein multilayer sheet of collagen material has a thickness of about 0.5-25 mm.
5. The method of item 1, wherein the chronic ulcer extends at least through the dermis and has been present for greater than 4 weeks.
6. The method of item 1, wherein the chronic ulcer extends at least through the hypodermis and has been present for greater than 6, 8, 10, 12, 24, or 40 weeks.

7. The method of item 1, further comprising applying a secondary dressing or re-dressing the chronic ulcer after step iv) is performed.

8. The method of item 1, further comprising applying sterile saline to remove a dressing material from the multilayer sheet of collagen material after step iv) is performed.

9. The method of item 1, further comprising changing the dressing over the implanted multilayer sheet of collagen material every 1 to 7 days after step iv) is performed.

10. The method of item 1, further comprising removing exudate from the chronic ulcer site every 1 to 7 days after step iv) is performed.

11. The method of item 1, further comprising inspecting the chronic ulcer every 1 to 7 days after step iv) and removing the dressing after a first visible epithelialization is observed at the chronic ulcer or removing the implanted multilayer sheet of collagen material and repeating steps i) to iv) if one or more of redness, swelling, hematomas, blistering, inflammation, excess exudate, infection, and necrosis are observed at the chronic ulcer.

12. The method of item 1, further comprising performing one or more of toe-blood pressure readings, pulse volume recordings, transcutaneous oxygen measurements, and skin perfusion pressure measurements.

13. The method of item 1, further comprising one or more of promoting neutrophils and monocytes to localize at the chronic ulcer site, promoting formation of a multi-layered cell structure in the ulcer site, promoting conversion of monocytes to macrophages, promoting secretion of the patient's own growth factors, promoting tissue proliferation and cell migration, promoting production and cross-linking of collagen at the chronic ulcer site, promoting growth of endothelial cells, promoting angiogenesis that was stalled at the chronic ulcer site, promoting formation of a vascular network and granulation, promoting oxygenation of the chronic ulcer site, and reducing one or more of purulent drainage, erythema, pain, warming, tenderness, induration, and bleeding at the chronic ulcer site.

14. A method of increasing liquid uptake capacity in a chronic ulcer of a subject in need thereof, comprising:
    i) aseptically implanting into the chronic ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer; and
    ii) hydrating the multilayer sheet of collagen material in dry state, thereby increasing liquid uptake capacity in the chronic ulcer.

15. The method of item 14, further comprising inhibiting exudate drainage, bleeding from the chronic ulcer, and preventing floating away of the multilayer sheet of collagen material out of the bed of the chronic ulcer.

16. A method of promoting hemostasis in a chronic ulcer of a subject in need thereof, comprising:
    i) aseptically implanting a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer; and
    ii) hydrating the implanted multilayer sheet of collagen material, thereby promoting hemostasis in the chronic ulcer.

17. The method of item 16, wherein blood clot formation in a chronic ulcer is accelerated by at least 2-fold compared to blood clot formation in a chronic ulcer in the absence of said implanted multilayer sheet of collagen material.

18. A method of binding and preserving a subject's growth own factors in a chronic skin ulcer of a subject in need thereof, comprising:
    i) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer; and
    ii) hydrating the implanted multilayer sheet of collagen material, thereby promoting binding of said subject's own growth factors with the multilayer sheet of collagen material and preservation of said subject's own growth factors and growth factor activity in the chronic skin ulcer thereby inducing expression of one or more growth factor-responsive genes in one or more human cell types in the chronic skin ulcer of the subject.

19. The method of item 18, wherein the growth factors are two or more of transforming growth factors (TGFs), fibroblast growth factors (FGFs), epidermal growth factor (EGF), Insulin-like Growth Factor (IGF-1), Platelet-derived Growth Factors (PDGFs), and vascular endothelial growth factors (VEGFs).

20. The method of item 18, wherein said one or more human cell types are human fibroblasts, human epidermal keratinocytes, human endothelial cells and human pluripotent stem cells.

21. A method of attracting one or more human cell types to a chronic skin ulcer of a subject in need thereof, comprising:
    i) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic skin ulcer; and
    ii) hydrating the implanted multilayer sheet of collagen material in dry state, thereby attracting one or more human cell types to the chronic skin ulcer.

22. The method of item 21, wherein said one or more human cell types are human fibroblasts, human epidermal keratinocytes, human endothelial cells and human pluripotent stem cells.

23. A method of promoting attachment and growth of one or more human cell types in a chronic skin ulcer of a subject in need thereof, comprising:
  i) aseptically implanting into the chronic ulcer of the subject a multilayer sheet of collagen material in dry state comprising (a) a barrier layer of collagen material having a smooth face and a rough face opposite said smooth face and (b) a spongeous matrix layer of collagen material connected to said fibrous face, said spongeous matrix layer of collagen material having an open sponge-like texture, such that the rough face of said barrier layer of collagen material to which is connected said spongeous matrix layer of collagen material having an open sponge-like texture faces toward and is adjacent to the bed of the chronic skin ulcer;
  ii) hydrating the multilayer sheet of collagen material in dry state;
  iii) promoting attachment and growth of one or more human cell types in the chronic skin ulcer; and
  iv) promoting proliferation of one or more human cell types in the chronic skin ulcer.

24. The method of item 23, wherein said one or more human cell types are human fibroblasts, human epidermal keratinocytes, human endothelial cells and human pluripotent stem cells.

25. A method of inhibiting one or more MMPs in a chronic skin ulcer of a subject in need thereof, comprising
  i) aseptically implanting into the chronic ulcer of the subject a multilayer sheet of collagen material in dry state comprising (a) a barrier layer of collagen material having a smooth face and a rough face opposite said smooth face and (b) a spongeous matrix layer of collagen material connected to said fibrous face, said spongeous matrix layer of collagen material having an open sponge-like texture, such that the rough face of said barrier layer of collagen material to which is connected said spongeous matrix layer of collagen material having an open sponge-like texture faces toward and is adjacent to the bed of the chronic skin ulcer; and
  ii) hydrating the implanted multilayer sheet of collagen material in dry state, thereby inhibiting MMPs and other collagenases in the chronic skin ulcer.

26. The method of item 25, wherein the MMPs are of MMP-1, MMP-2, MMP-3, MMP-8, and MMP-9.

27. The method of any one of items 1-26, wherein the subject suffers from a venous ulcer, a vascular ulcer, an arterial ulcer, a diabetic ulcer, a decubitus ulcer, a peripheral vascular disease, cellulitis, osteomyelitis, an ulcer at a surgical site, dehiscence, or a combination thereof.

28. The method of any one of items 1-26, wherein the subject suffers from venous leg ulcers, diabetic foot ulcers, pressure ulcers, or a combination thereof.

29. The method of any one of items 1-26, wherein the subject suffers from diabetic foot ulcer (DFU) or venous leg ulcer (VLU).

30. The method of any one of items 1-26, wherein the subject suffers from diabetes, metabolic disorders, thyroid malfunction or dysfunction, and/or an autoimmune disease.

31. The method of any one of items 1-26, wherein the subject suffers from hyperglycemia, neuropathy, vasculopathy, infection, fibrin cuff, and/or venous hypertension.

32. The method of any one of items 1-26, wherein the subject has been or is being treated with corticosteroid therapy, is undergoing radiation therapy, is receiving anticoagulation therapy, chemotherapy, or uses drugs, alcohol, tobacco, or other agents that disrupt a normal ulcer healing process.

33. The method of any one of items 1-32, further comprising treating the subject with compression therapy, vacuum assisted closure (VAC), offloading, negative pressure, hyperbaric oxygen therapy, or a combination thereof.

34. The method of any one of items 1-33, wherein the multilayer sheet of collagen material in dry state has physical properties such that it absorbs about 7 to about 12 times its weight of biological fluids.

35. The method of any one of items 1-34, wherein the multilayer sheet of collagen material has been gamma-sterilized, or X-ray sterilized.

36. The method of any one of items 1-35, wherein the multilayer sheet of collagen material has not been artificially cross-linked, has not had any growth factors or other ulcer-treating agents added to it, and/or has not had any antimicrobial agents added to it.

37. The method of any one of items 1-36, further comprising, after 4 to 7 days, removing at least a portion of the implanted multilayer sheet of collagen material and repeating the method steps.

38. The method of any one of items 1-37, further comprising providing a pH of about 3 to about 6.7 or about 3.5 to about 6.25, or about 4 to about 5.5, or about 4.1 to about 5.1, or about 4.15 to about 4.95, or any pH in any of the recited ranges, in the chronic ulcer site, 39. A method of treatment comprising manufacturing a kit comprising providing a pouch having a blister, aseptically sealing a multilayer sheet of collagen material in dry state comprising (i) a barrier layer of collagen material having a smooth face and a rough face opposite said smooth face and (ii) a spongeous matrix layer of collagen material connected to said fibrous face, said spongeous matrix layer of collagen material having an open sponge-like texture, in the blister, and combining the pouch having the blister and multilayer sheet of collagen material sealed therein with instructions for use of the multilayer sheet of collagen material of the present disclosure in a box, wherein the instructions for use require a user to take specific actions including a plurality of the following: aseptically trimming the multilayer sheet of collagen material to the desired size and/or shape to form an implant; using a scalpel, shears, scissors, and/or graspers to trim and/or shape the multilayer sheet of collagen material to form an implant; applying the multilayer sheet of collagen material to the chronic ulcer site with the lower layer facing the chronic ulcer; directly applying the multilayer sheet of collagen material to the chronic ulcer site in a dry state; storing the multilayer sheet of collagen material at a temperature of between about 10 to about 30° C. prior to the implanting step; implanting the multilayer sheet of collagen material in the chronic ulcer and then completely hydrating the multilayer sheet of collagen material in situ using blood, sterile saline solution, or a combination thereof to hydrate the multilayer sheet of collagen material; and applying a first dressing that covers the chronic ulcer site having the multilayer sheet of collagen material implanted therein.

40. The method of item 39, wherein the instructions for use require a user to take further specific actions including a plurality of the following: providing a hydrocolloid dressing over the chronic ulcer site having the multilayer sheet of collagen material implanted therein; applying a secondary dressing or re-dressing the chronic ulcer site; applying a non-adhesive secondary dressing or re-dressing; applying sterile saline to remove a dressing material from the multilayer sheet of collagen material; changing the dressing over the implanted multilayer sheet of collagen material every 1 to 7 days after implantation; changing the secondary dressing over the first dressing every 1 to 7 days after implantation; removing exudate from the chronic ulcer site every 1 to 7 days after implantation; monitoring the size, shape, color, inflammation, and drainage of the edges of the chronic ulcer site every 1 to 7 days after implantation; removing the implanted multilayer sheet of collagen material and repeating the implanting step; ensuring that the chronic ulcer site is free of acute infection before implanting the multilayer sheet of collagen material; treating infections at or near the chronic ulcer site prior to implanting the multilayer sheet of collagen material; identifying patients with allergies or sensitivities to porcine or collagen materials prior to implanting the multilayer sheet of collagen material; and not implanting the multilayer sheet of collagen material in patients that have allergies or sensitivities to porcine or collagen materials.

The following Examples are merely illustrative and are not intended to limit the scope of the present disclosure in any way.

Example 1: Preparation of the Multilayer Sheet of Collagen Material

Peritoneal membranes from pigs were purified to be completely free from flesh and grease by mechanical means, washed under running water and treated with 2% NaOH solution for 12 hours. The membranes were then washed under running water and acidified with 0.32% HCl. After the material had been acidified through its entire thickness (for about 15 minutes) the material was washed with water until a pH of 3.5 was obtained. The material was then shrunk with 7% saline solution, neutralised with 1% $NaHCO_3$ solution and washed under running water. The material was then dehydrated with acetone and degreased with n-hexane and dried using ethanol ether to obtain a purified collagen material membrane (A) in dry state having a smooth face acting as a barrier to prevent passage of cells therethrough and a rough fibrous face opposite said smooth face. That purified collagen material membrane (A) in dry state had a water content of 5-20% as determined by Karl-Fischer titration according to Ph. Eur. 2.5.12A, USP <921>.

Porcine hides were ground in a meat grinder to pieces of 1 to 20 mm. Water was removed from the ground porcine hides using a water-soluble solvent such as an alcohol or a ketone. The collagen fibers were defatted using a chlorinated hydrocarbon such as dichloroethane or methylene chloride, a non-chlorinated hydrocarbon such as hexane or toluene, or an ether such as TBME (tertbutyl methyl ether). After removing the solvent, the collagen material was treated with a strong inorganic base (e.g., an inorganic base having a pKa of greater than 10) at a pH above 12 for a period of 6 to 24 hours and treated with a strong inorganic acid (e.g., an inorganic acid having a pKa of less than 0) at a pH of 0 to 1 for a period of 1 to 12 hours. The excess acid was removed by rinsing with water and the suspension was homogenized to a 0.5 to 2% homogenous suspension of collagen material in the presence of a swelling regulator such as an inorganic salt. The suspension was dried by freeze-drying and the dry collagen material was successively cleaned with different organic solvents such as alcohols, ethers, ketones and chlorinated hydrocarbons. The solvents were then evaporated under vacuum to a solvent residue of less than 1%. A slurry of collagen material was prepared by mixing the cleaned dry collagen material obtained above with acidified water to obtain a new slurry of collagen material (B) containing about 1.5% collagen material and about 0.9% sodium chloride.

The slurry of collagen material (B) was poured on the fibrous face of the purified collagen material membrane (A) in dry state, or alternatively, the slurry of collagen material (B) was poured in a recipient and the fibrous face of the purified collagen material membrane (A) in dry state was laid on top of the slurry of collagen material, the w/w ratio of slurry of collagen material (B) to the purified collagen material membrane (A) in dry state being generally from 25/1 to 1/5, usually from 15/1 to 1/2. After about 30 minutes, the combined product was freeze-dried such as to obtain a multilayer sheet of collagen material in dry state comprising (i) a barrier layer of collagen material having a smooth face and a fibrous face opposite said smooth face (part of the multilayer sheet of collagen material coming from the purified collagen membrane (A)) and (ii) a spongeous matrix layer of collagen material connected to said fibrous face, said spongeous matrix layer having an open sponge-like texture. That multilayer sheet of collagen material in dry state had a water content of 5-20% as determined by Karl-Fischer titration according to Ph. Eur. 2.5.12A, USP <921>.

The pH of the multilayer sheet of collagen material was determined in water according to Ph. Eur. 2.2.3, USP <791>, using 0.01 g/ml sample material in water. Additionally, the material was incubated in a phosphate buffered saline (PBS) solution for 48 hours to simulate physiologic conditions. pH measurements were taken of the extraction solutions following 48 hours incubation. Measurement of pH extract solutions was utilized to assess the potential impact of multilayer sheet of collagen material on the ulcer environment. Following 48 hours of incubation, the pH of multilayer sheet of collagen material extract in water was 4.11±0.14 and 6.32±0.08 in PBS. PBS control pH was 7.4.

Example 2: Liquid Uptake Experiments

Figure 5:
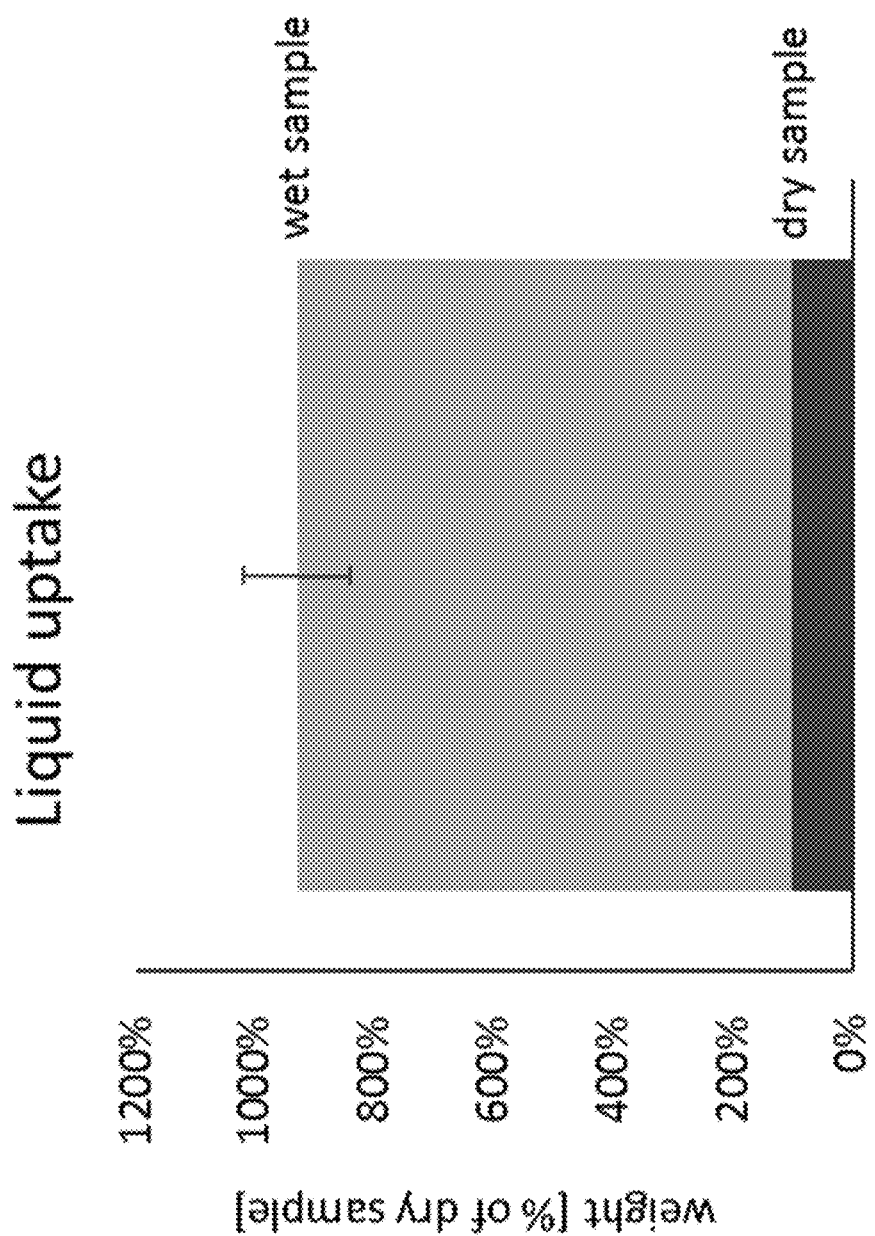
FIG. 5 is a graph showing the liquid uptake capacity by capillarity of the multilayer sheet of collagen material according to one aspect of the present disclosure.

Starting with multilayer sheet of collagen material in dry state obtained according to Example 1, the lower part of the material was soaked in phosphate buffered saline (PBS) and the liquid uptake capacity by capillarity was measured until the sample was completely hydrated. The liquid uptake capacity was calculated by dividing the weight of the wet sample by the weight of the dry sample. As shown in FIG. 5, the liquid uptake capacity of the multilayer sheet of collagen material according to Example 1 was such that the weight of the wet multilayer sheet of collagen material was 9.3±0.9 times the weight of the multilayer sheet of collagen material in dry state. These results confirm that the multilayer sheet of collagen material according to Example 1 absorbs a relatively large volume of physiological fluids present in the chronic ulcer site and suggest that the multilayer sheet of collagen material is prevented from being flushed away by fluids present in excess in the chronic ulcer site.

Example 3: Cell Culture and Cell Attachment and Cell Growth Assays

Adult human dermal fibroblasts (aHDF, ScienCell Research Laboratories) were cultured in complete cell culture medium consisting of Dulbecco's modified Eagle's medium (DMEM) containing 10% fetal bovine serum (FBS)

and 1% Penicillin/Streptomycin solution (both GIBCO, Life Technologies Corp.). Basal media used in cell treatments were prepared by adding only the penicillin/streptomycin component to DMEM and excluding the serum supplement. Neonatal human epidermal keratinocytes (HEKs) were obtained from LifeTechnologies and cultured in EpiLife medium (LifeTechnologies, Switzerland) supplemented with 1× Human Keratinocyte Growth Supplement (HKGS, LifeTechnologies). HEKs were cultured as per product instructions.

For co-culture experiments, angiogenesis-tested aHDF and HUVECs (both Caltag Medsystems, United Kingdom) were cultured and expanded as per product instructions for the Vasculogenesis to Angiogenesis (V2a) Kit (Caltag Medsystems, United Kingdom).

aHDFs were seeded onto the upper layer of the multilayer sheet of collagen material at a concentration of 50000 cells in 50 µl medium per scaffold. Extra medium was added after 1 h at room temperature. Culture conditions were maintained at 37° C., 5% $CO_2$, and humid atmosphere, with medium changed three times per week. At defined time points, medium was removed and the scaffolds were washed in PBS, fixed with 10% neutral-buffered formalin (PFA; Sigma-Aldrich), and permeabilized with a 10 min incubation in 0.1% Triton X-100/PBS (Sigma-Aldrich). Scaffolds were washed in PBS at each intermediate step. Cytoskeletal actin staining was performed with Alexa Fluor® 488 Phalloidin (Molecular Probes) diluted 1:80 in 1% bovine serum albumin/PBS (Sigma-Aldrich). Sections were imaged using a Yokogawa CV1000 Cell Voyager confocal microscope. The pictures obtained are represented in FIGS. 6A and 6B.

For co-culture experiments, angiogenesis-tested HUVECs and aHDF (both Caltag Medsystems) were seeded onto the smooth face of the multilayer sheet of collagen material at a concentration of 40,000 cells in 50 µl medium per scaffold, at a ratio 1:9. Extra medium was added after 1 h at room temperature. Culture conditions were maintained at 37° C., 5% CO2, and humid atmosphere, with medium changed three times per week, as per product instructions (V2a, Caltag Medsystems). After 14 days in culture, medium was removed and the scaffolds were washed in PBS, fixed with 10% PFA (Sigma-Aldrich), and permeabilized with a 10 min incubation in 0.5% Triton X-100/PBS (Sigma-Aldrich). Scaffolds were washed in PBS at each intermediate step. CD-31 staining was performed with primary mouse antibody (Dako) diluted 1:50 in 1% BSA/PBS for 2 h at RT. Fluorophore-coupled goat anti-mouse antibody (Molecular Probes) was diluted 1:1000 in BSA/PBS and incubated for 1 h at RT. Cytoskeletal actin staining was performed in parallel with Alexa Fluor® 488 Phalloidin (MolecularProbes) diluted 1:80 in 1% bovine serum albumin/PBS (Sigma-Aldrich). Additionally, the cell nuclei were stained using a 1:2000 dilution of DAPI in PBS (MolecularProbes). Samples were imaged using a Yokogawa CV1000 Cell Voyager confocal microscope. The pictures obtained are represented in FIG. 6C.

For full thickness skin equivalent co-culture experiments, human keratinocytes and aHDFs (obtained from CELLnTEC AG, Switzerland) were seeded onto the smooth face of the multilayer sheet of collagen material, according to the manufacturers' instructions (CELLnTEC AG, Switzerland). At the end of culture, samples were fixed with 10% PFA (Sigma-Aldrich) and histological sections were prepared and stained by an independent contract research organization (Morphisto, Germany). The pictures obtained are represented in FIGS. 7A and 7B.

Figure 6A:
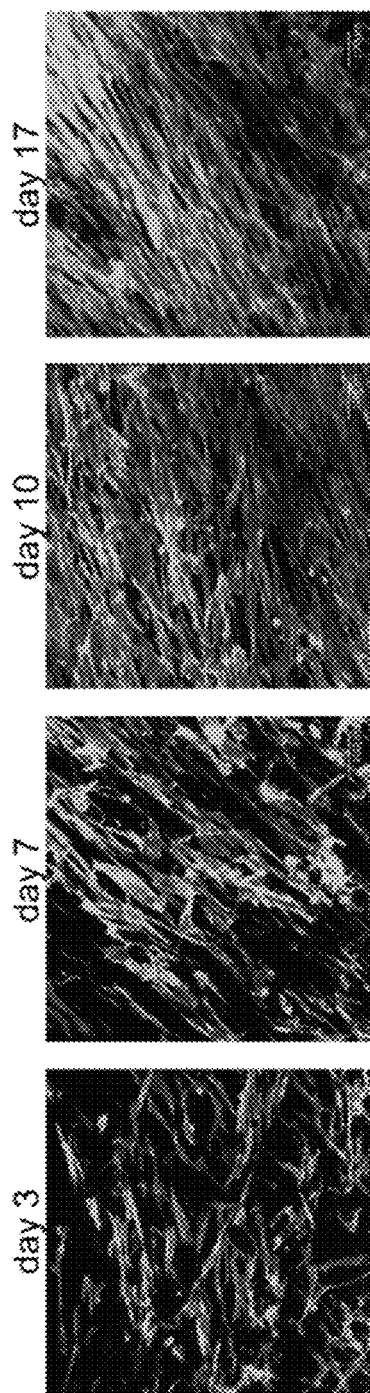
FIG. 6A shows attachment and proliferation of adult human dermal fibroblasts fluorescently labelled with phalloidin after 3, 7, 10, and 17 days in culture, respectively.
Figure 6B:
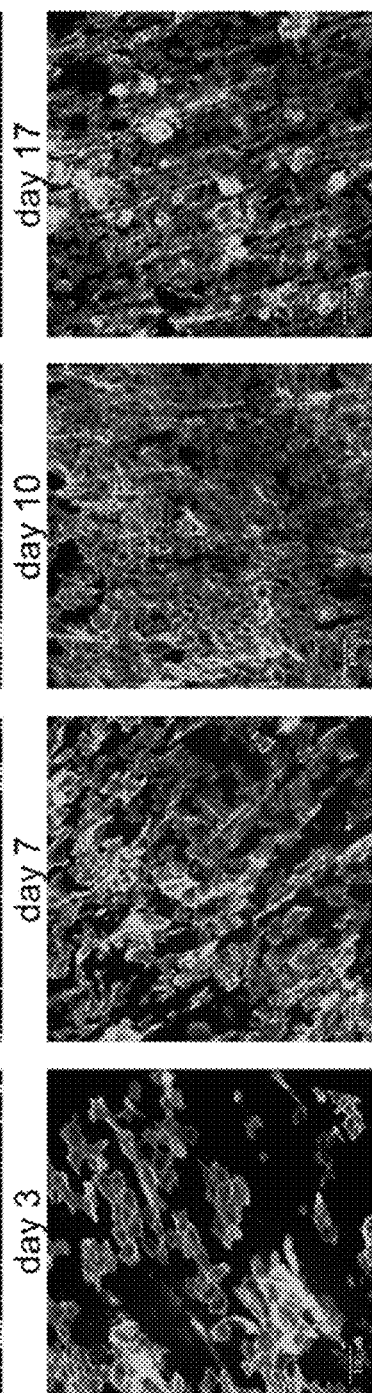
FIG. 6B shows attachment and proliferation of human epidermal keratinocytes fluorescently labelled with phalloidin after 3, 7, 10, and 17 days in culture, respectively.

As shown in FIG. 6A, the multilayer sheet of collagen material prepared according to Example 1 was seeded with the adult human dermal fibroblasts and fluorescently labelled with phalloidin after days 3, 7, 10, and 17. The staining demonstrates that the adult human dermal fibroblasts attached and proliferated on the multilayer sheet of collagen material. As shown in FIG. 6B, the multilayer sheet of collagen material prepared according to Example 1 was seeded with human epidermal keratinocytes and fluorescently labelled with phalloidin after days 3, 7, 10, and 17. The staining demonstrates that the human epidermal keratinocytes attached and proliferated in the multilayer sheet of collagen material.

Figure 6C:
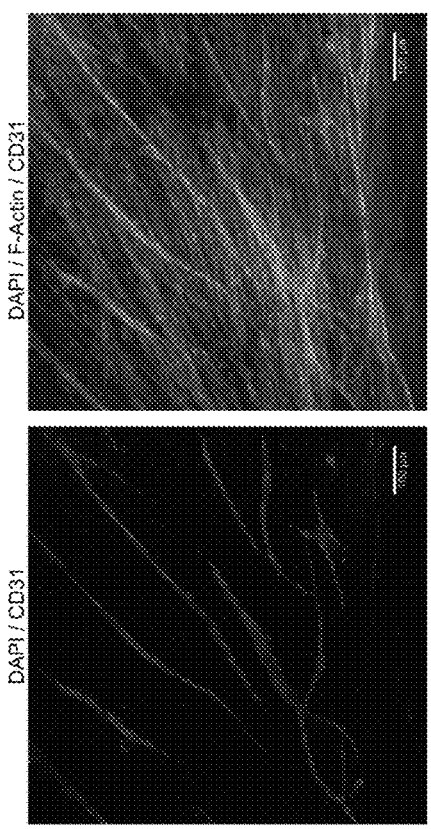
FIG. 6C shows a co-culture of human dermal fibroblasts and human umbilical vein endothelial cells (HUVECs) fluorescently labeled with 4',6-diamidino-2-phenylindole (DAPI) and anti-human CD31 antibody (left image) and with DAPI, Phalloidin and anti-human CD31 antibody (right image), after 14 days in culture, respectively.

FIG. 6C shows a co-culture of human dermal fibroblasts and human umbilical vein endothelial cells (HUVECs) fluorescently labeled with 4',6-diamidino-2-phenylindole (DAPI) and anti-human CD31 antibody (left image) and with DAPI, Phalloidin and anti-human CD31 (right image). The multilayer sheet of collagen material prepared according to Example 1 was shown to serve as a suitable collagen scaffold for cell attachment and growth and allowed a mixture of adult human dermal fibroblasts and human umbilical vein endothelial cells to build a network of blood vessel-forming cells.

Figure 7B:
FIG. 7B shows a full thickness skin model of human dermal fibroblasts and human epidermal keratinocytes seeded on the multilayer sheet of collagen material according to one aspect of the present disclosure after 14 days in culture.
Figure 7A:
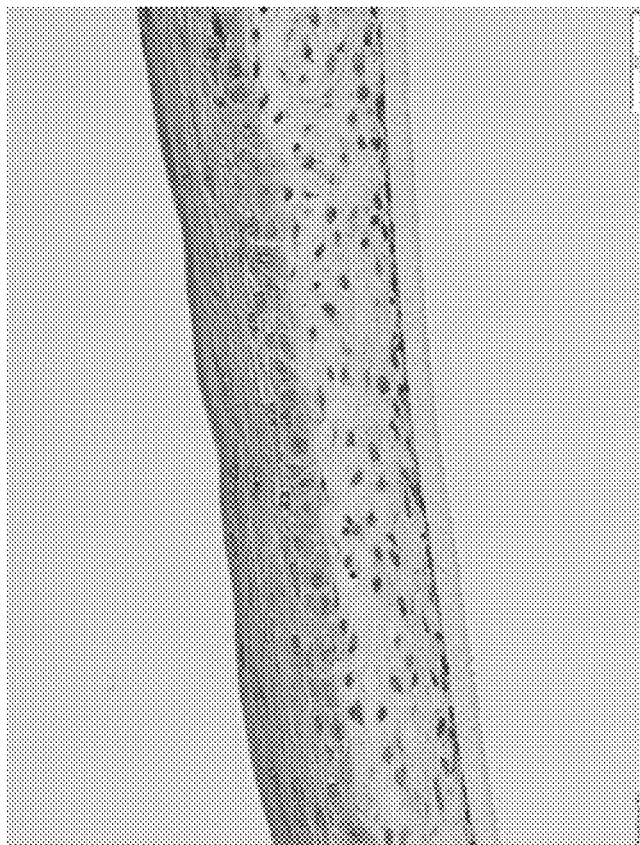
FIG. 7A shows a full thickness skin model of human dermal fibroblasts and human epidermal keratinocytes seeded on a filter membrane.

As shown in FIG. 7B, the multilayer sheet of collagen material according to the present disclosure serves as a suitable matrix for cell attachment and growth as well as a substrate for a full thickness skin equivalent.

Example 4: Growth Factor Response Assays

Human cells were seeded onto washed multilayer sheet of collagen material according to Example 1 that was previously soaked in physiological solutions containing recombinant human growth factors. Gene expression analysis showed cell responses specific to active TGF-b1, bFGF, and VEGF. TGF-b1 contributes in the inflammatory phase and is involved with granulation tissue formation, re-epithelialization, matrix formation and remodeling. bFGF accelerates wound healing and functions in granulation tissue formation, re-epithelialization, matrix formation and remodeling. VEGF effects on multiple components of the wound healing cascade, including tissue granulation, angiogenesis and epithelization and collagen deposition.

The multilayer sheet of collagen material of the present disclosure was cut in pieces of ~8×8 mm and incubated 4 h with recombinant human TGF-b1 (50 ng/ml), recombinant human bFGF (50 ng/ml), or recombinant human VEGF (100 ng/ml), respectively (all R&D systems, Switzerland), diluted in PBS or cell culture medium. After incubation, membranes were vigorously washed four times for 15 minutes with respective solution. aHDF for TGF-b1 and bFGF-treated membranes and HUVECs for VEGF-treated membranes, respectively, were seeded onto the smooth side of the multilayer sheet of collagen material with a concentration of 50,000 cells per sample. In indicated experiments, cells were seeded directly onto the plate and membranes were placed on top of the well avoiding contact with the cells to evaluate incomplete washing of the membrane. After 1 h (VEGF), 24 h (bFGF), and 48 h (TGF-b1), respectively, cells were lysed and RNA was extracted.

Growth factor target genes were selected for analysis: KANK4 (Hs01057354_m1) for TGF-b1, EGR3 (Hs04935588_m1) for VEGF, and MMP-1 (Hs00899658_m1) for bFGF, and glyceraldehyde 3-phosphate dehydrogenase (GAPDH) (Hs02758991_g1) as a reference. Total RNA was prepared with TriZol (Life Technologies, Switzerland), and 500 μg were used for reverse transcription (RT) with Aurum Total RNA Mini Kit (Bio-Rad, Switzerland). PCR was performed with the Light Cycler 480 Probes Master (Roche, Switzerland) on a CFX connect PCR System (Bio-Rad). TaqMan probes were purchased from Applied Biosystems. The mRNA levels were calculated by normalizing to the housekeeping gene GAPDH.

Figure 8A:
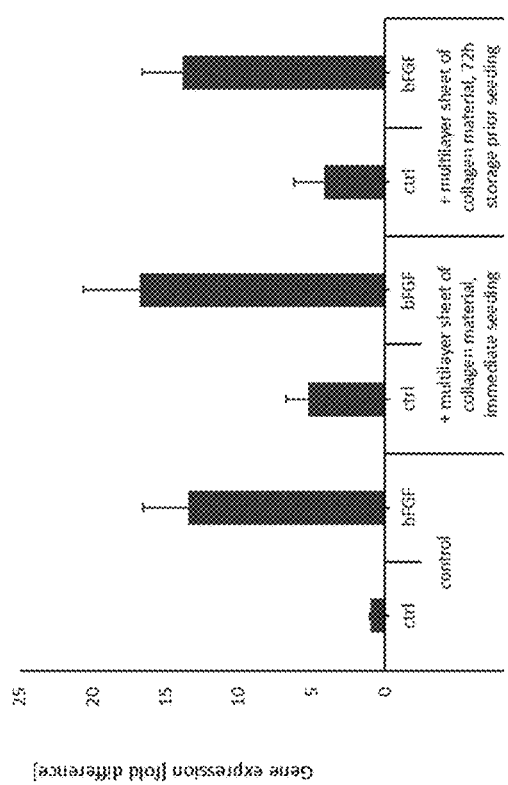
FIG. 8A shows the KN Motif and Ankyrin Repeat Domains 4 (KANK4) gene expression in adult human fibroblasts in response to TGF-b1 with or without the multilayer sheet of collagen material.
Figure 8B:
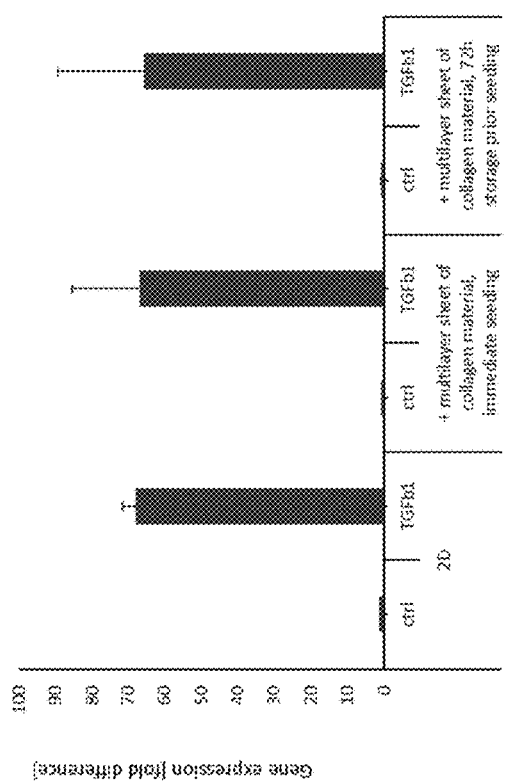
FIG. 8B shows the MMP-1 gene expression in adult human fibroblasts in response to bFGF with or without the multilayer sheet of collagen material.
Figure 8C:
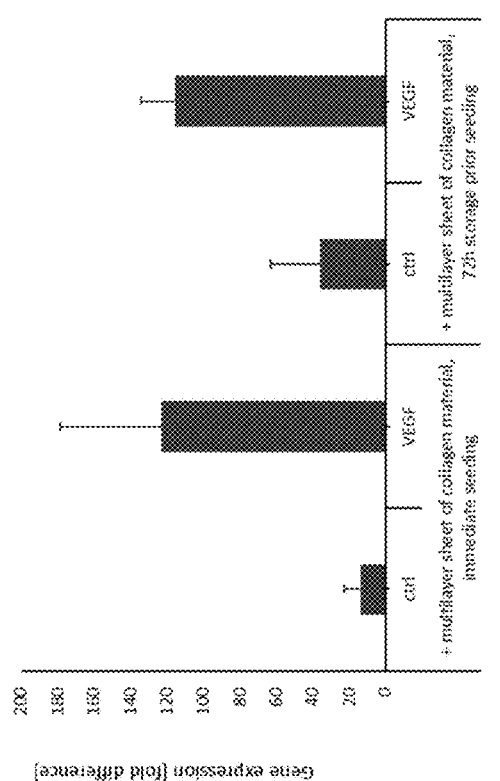
FIGS. 8C and 8D show the EGR3 gene expression response in human umbilical vein endothelial cells in response to VEGF with or without the multilayer sheet of collagen material.
Figure 8D:
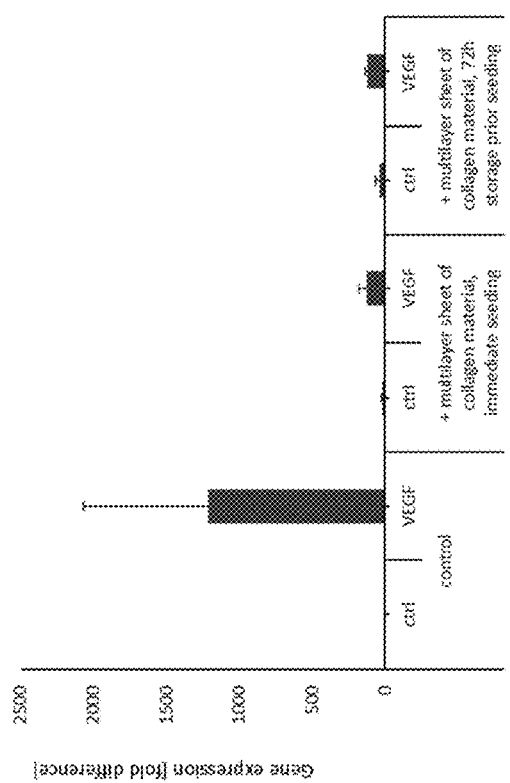

Gene expression of growth factor-responsive genes was induced in adult human dermal fibroblasts and human umbilical vein endothelial cells grown on washed multilayer sheet of collagen material according to Example 1 previously soaked in physiological solutions containing recombinant human growth factors. FIG. 8A shows the KN Motif And Ankyrin Repeat Domains 4 (KANK4) response to TGF-b1. FIG. 8B shows the MMP-1 response to bFGF. FIGS. 8C and 8D show the EGR3 response to VEGF. Immediate refers to the gene expression response in cells seeded onto the multilayer sheet of collagen material immediately after washing. 72 hours refers to the gene expression in cells seeded onto the multilayer sheet of collagen material after washing and storage for 72 hours.

As shown in FIG. 8A, response to TGF-b1 was preserved when washed multilayer sheet of collagen material according to Example 1 was stored for 72 h before seeding. As shown in FIG. 8B, response to bFGF was preserved. As shown in FIGS. 8C and 8D, response to VEGF was preserved.

These findings demonstrate that the multilayer sheet of collagen material according to Example 1 rapidly adsorbs bioactive TGF-b1, bFGF, and VEGF present in physiological solutions and preserves growth factor activity during storage.

Example 5: Tissue Extracts

To prepare soluble extracts for cell culture experiments, the multilayer sheet of collagen material according to Example 1 was minced, yielding approximately ~1×1 mm pieces of tissue, which were extracted at 10 mg dry tissue/ml in basal media appropriate for the cell type to be evaluated. After overnight extraction at 37° C., the tissue residue was removed by centrifugation at 3220 RCF for 5 minutes at room temperature, and the extract was sterile filtered using a 0.22 mm filter unit.

Example 6: Proliferation Studies on Human Dermal Fibroblasts

Adult human dermal fibroblasts were plated at a density of 2500 cells/well on 96-well plates in complete cell culture medium. After 24 hours, the medium was aspirated from the wells and replaced with one of the following: DMEM lacking serum (negative control), DMEM plus FBS (positive control), or medium containing extracts of the multilayer sheet of collagen material of the present disclosure at 0.5, 1, 2, and 5 mg/mL, both with and without FBS supplement. Extracts were prepared by making serial dilutions of the original 10 mg/mL extract prepared according to Example 5 in basal medium, and supplemented with FBS where indicated. After 72 hours, a CyQuant assay (Molecular Probes CyQuant, Life Technologies C7026) was performed according to the manufacturer's instructions to quantify DNA content (n=6 replicates of samples per treatment) as a measure of cellular proliferation. DNA content was quantified by use of a fluorescence plate reader (excitation 485 nm/emission 528 nm). Direct cell number was quantified by detecting CyQuant-labelled nuclei in IncuCyte FL. Fluorescent nuclei per image were counted and the cell number per well was calculated.

Cell were grown in Dulbecco's modified Eagle's medium (DMEM) containing 0% FBS (FIG. 9A) or 10% FBS (FIG. 9B), respectively. The multilayer sheet of collagen material extract concentration in the respective DMEM formulation is shown on the x-axis. Each value represents the average±standard deviation of 3 batches, each analyzed in 3 independent experiments with n=6 six wells per experiment. ($p<0.001$ compared to control and compared to all other concentrations of the multilayer sheet of collagen material; *, $p<0.05$ compared to control and compared to 0.5 mg/ml).

Figure 9A:
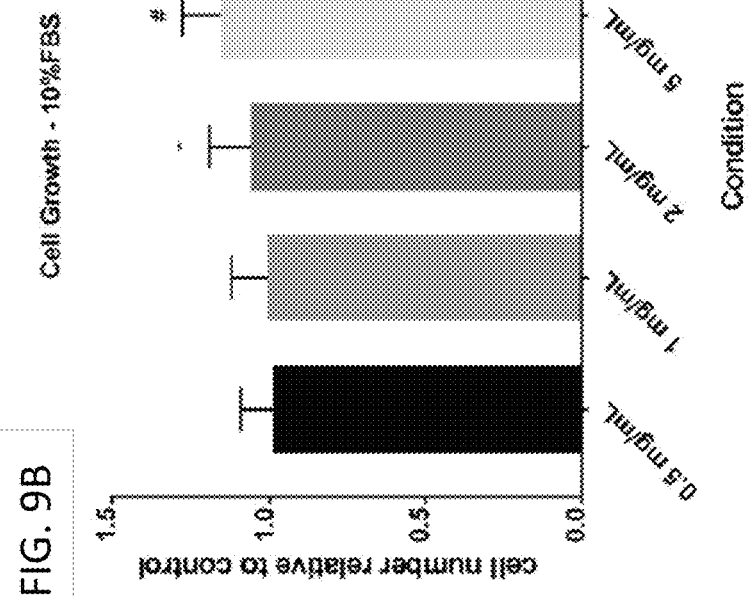
FIG. 9A shows the dose-dependent increase in adult human dermal fibroblast (aHDF) proliferation in serum free basal cell culture media containing extracts of the multilayer sheet of collagen material.
Figure 9B:
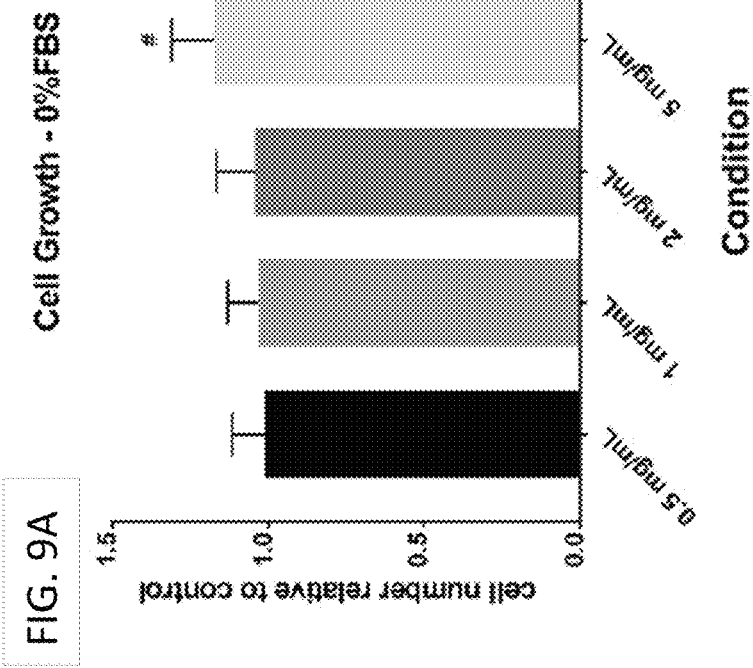
FIG. 9B shows the dose-dependent increase in adult human dermal fibroblast (aHDF) proliferation in cell culture media containing 10% fetal bovine serum (FBS) and extracts of the multilayer sheet of collagen material.

Extracts of the multilayer sheet of collagen material prepared according to Example 5 caused a dose-dependent increase in adult human dermal fibroblast (aHDF) proliferation in both basal and complete cell culture media (FIGS. 9A and B). The largest proliferative effect was observed for the 5 mg/ml concentration of the extract, where cell number increased significantly. These results establish (i) that components will elute from the multilayer sheet of collagen material under physiological conditions and (ii) that the multilayer sheet of collagen material components cause aHDF to proliferate.

Example 7: Trans-Well Migration Assays

Trans-well migration assays were performed as described in J. Tissue Eng. Regen, Med. 2008 Dec. 2(8): 491-498

In vitro trans-well migration of HEK toward extracts of the multilayer sheet of collagen material of the present disclosure was evaluated using xCELLigence RTCA DP Real Time Cell Analyzer (Acea Biosciences), according to manufacturer's instructions. When HEK reached 70-80% confluency, they were starved for 3 hours in unsupplemented EpiLife medium before use in trans-well migration assays. Then, HEK were trypsinized, neutralized, and centrifuged as per HEK product instructions, and resuspended in unsupplemented EpiLife medium.

The extracts of the multilayer sheet of collagen material of the present disclosure prepared according to Example 5 in unsupplemented EpiLife medium were further diluted in unsupplemented EpiLife medium to concentrations of 0.5, 2, and 5 mg/ml. Unsupplemented EpiLife medium served as negative control. A positive control of 10% HKGS in unsupplemented EpiLife medium was also included in each assay. Samples were loaded to the lower chamber of each well of the BD plate, the plate was assembled and 50 uL of unsupplemented EpiLife medium was added to the upper chamber of each well. The plate was equilibrated for 1 h at 37° C. Then, background measurement was performed. Approximately 30,000 cells were added to the upper chamber of each well in 100 uL of ussupplemented EpiLife medium. The trans-well migration chamber was incubated at 37° C. for 16 hours. Trans-well migration was recorded through determination of cell index every 5 minutes; cell index data after 12 hours were recorded. After 16 hours, cells were fixed with 100% ethanol, and stained with DAPI or crystal violet, respectively, to confirm migrated cells in the lower chamber. Keratinocyte migration was further confirmed using 2 mm diameter disks of the multilayer sheet of collagen material of the present disclosure instead of soluble extract of the multilayer sheet of collagen material of the present disclosure.

Figure 10A:
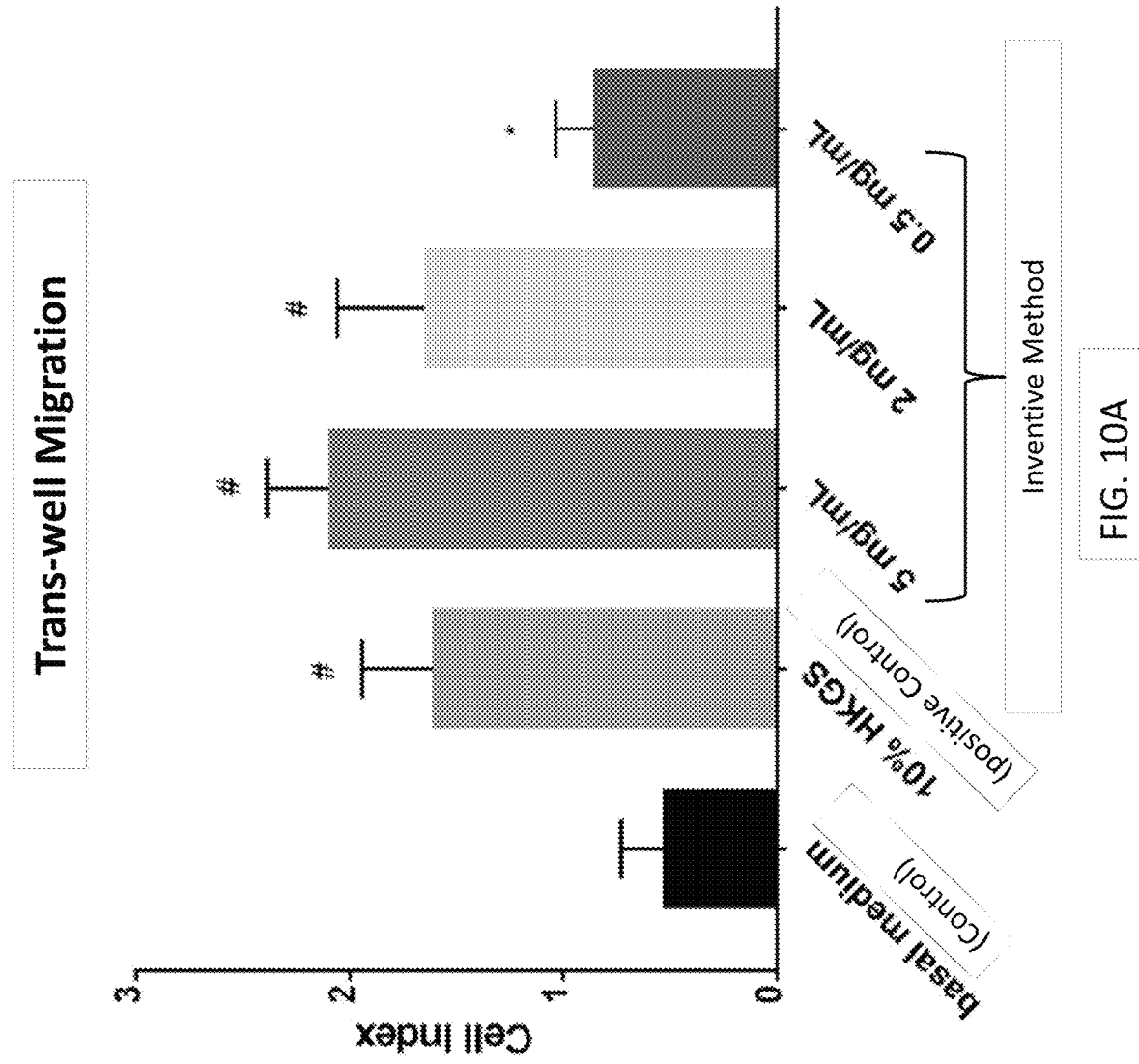
FIG. 10A is a graph showing the effects of extracts of the multilayer sheet of collagen material on epidermal keratinocyte trans-well migration.

FIG. 10A shows the effects of extracts of the multilayer sheet of collagen material on human epidermal keratinocyte trans-well migration. Each value represents the average±standard deviation of 2 batches of the multilayer sheet of collagen material, each analyzed in 3 independent experiments with n=4 six wells per experiment. #, $p<0.001$ compared to basal medium; *, $p<0.05$ compared to basal medium. Cell indexes were confirmed with crystal violet staining (FIG. 10B). Keratinocyte migration was further confirmed using 2 mm diameter disks of the multilayer sheet of collagen material of the present disclosure instead of soluble extract of the multilayer sheet of collagen material of the present disclosure (FIG. 10C). The cell index observed in the multilayer sheet of collagen material disks was significant compared to negative control conditions and similar to positive control samples. Thus, multilayer sheet of collagen material tissue in the culture medium was capable of directing keratinocyte migration in vitro.

Samples of unsupplemented basal medium containing 0.5, 2, and 5 mg/ml of extracts from multilayer sheet of collagen material, respectively, demonstrated significantly greater human epidermal keratinocyte (HEK) migration compared with basal medium alone. The experimental groups containing 2 and 5 mg/ml of the extract of the multilayer sheet of collagen material reached or even exceeded the number of cells detected in positive controls (10% HKGS). These results demonstrated that the multilayer sheet of collagen material in the basal culture medium was capable of directing significant HEK migration in vitro.

Example 8: MMP Activity Assays

Samples of the multilayer sheet of collagen material of the present disclosure were incubated with solutions containing elevated protease activity (EPA). Using fluorometric assays, matrix metalloproteases (MMPs) activity was measured over time. Samples were incubated in solutions containing human recombinant MMP-2, MMP-9, and MMP-1. After 2 hours, supernatant extracts were mixed with fluorogenic substrate and protease activity was measured kinetically. Specifically, multilayer sheet of collagen material according to the present disclosure was cut in pieces weighing between 3 and 4 mg. Human recombinant MMPs (R&D Systems) were activated with p-aminophenylmercuric acetate. 100 ng activated rhMMP (at 2 ng/µl in buffer) were added per mg of multilayer sheet of collagen material and incubated at 37° C. with shaking. After 2 h of incubation, residual enzymatic activity in the supernatant was measured by adding the fluorogenic substrate Mca K P L G L Dpa-A-R-NH2 (R&D Systems) to an aliquot. Relative fluorescence units were read in kinetic mode with a microplate reader (Synergy H1, BioTek). Residual MMP activity was determined by comparing Vmax of the multilayer sheet of collagen material supernatant relative to Vmax of an untreated control and expressed as percentage activity.

Figure 11:
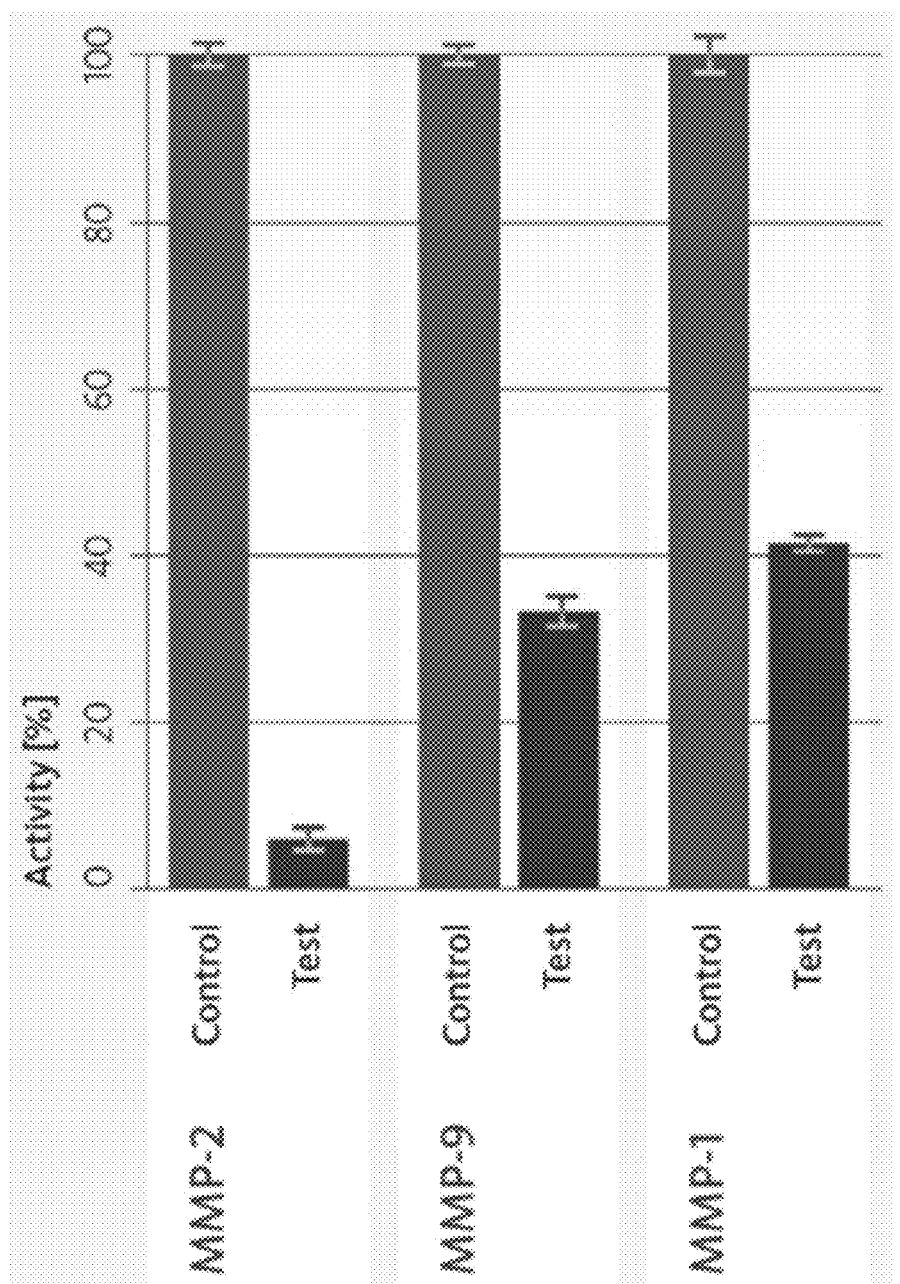
FIG. 11 shows the effect of the multilayer sheet of collagen material of the present disclosure on reducing MMP activity.

As shown in FIG. 11, the multilayer sheet of collagen material of the present disclosure ("Test") is effective at reducing elevated protease activity. A reduction in protease activity may help rebalance the chronic ulcer site by protecting growth factors and new tissue from MMPs, which in turn can facilitate healing. Each value represents the average±standard deviation of 1 batch of multilayer sheet of collagen material, each analyzed in 2 independent experiments with n=2 six wells per experiment.

Example 9: Hemostasis Assays

Figure 12:
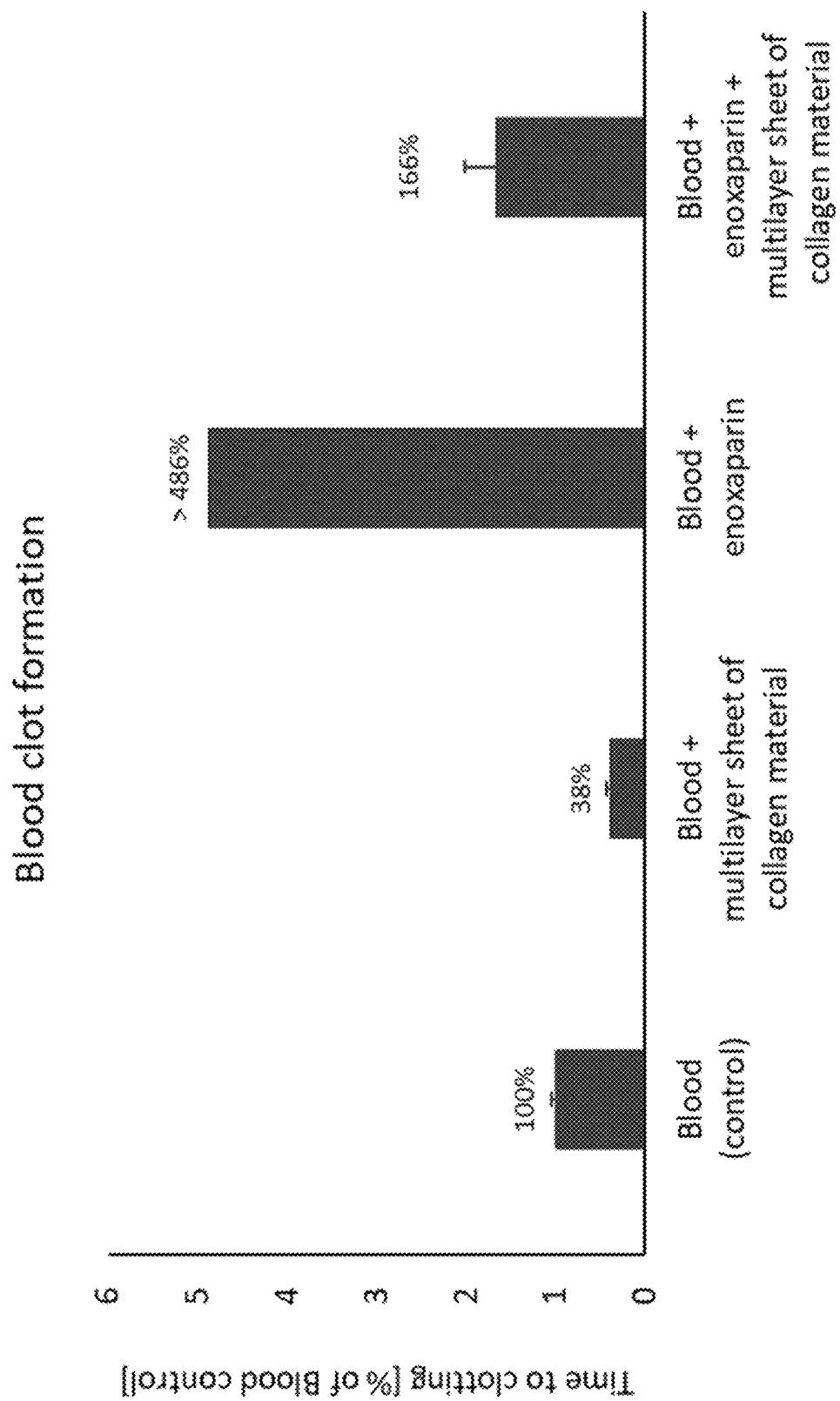
FIG. 12 shows the effects of the multilayer sheet of collagen material of the present disclosure on blood clot formation, in the presence or absence of Enoxaparin, a low molecular weight heparin.

Pulled apart multilayer sheet of collagen material of the present disclosure was mixed with native human blood at a ratio of 5 mg of the material per ml of blood by inverting a 15 ml polystyrene tube twice, and incubated at 37° C. The tubes were inverted once every minute until coagulation was observed and the respective time was recorded in FIG. 12. As a control, the time to clotting of blood in the absence of the multilayer sheet of collagen material of the present disclosure was observed and recorded in FIG. 12. Further, blood was tested in the presence of 1 IU/ml of the anti-factor Xa compound enoxaparin with or without the multilayer sheet of collagen material of the present disclosure and the time to clotting was observed and recorded in FIG. 12.

Figure 13:
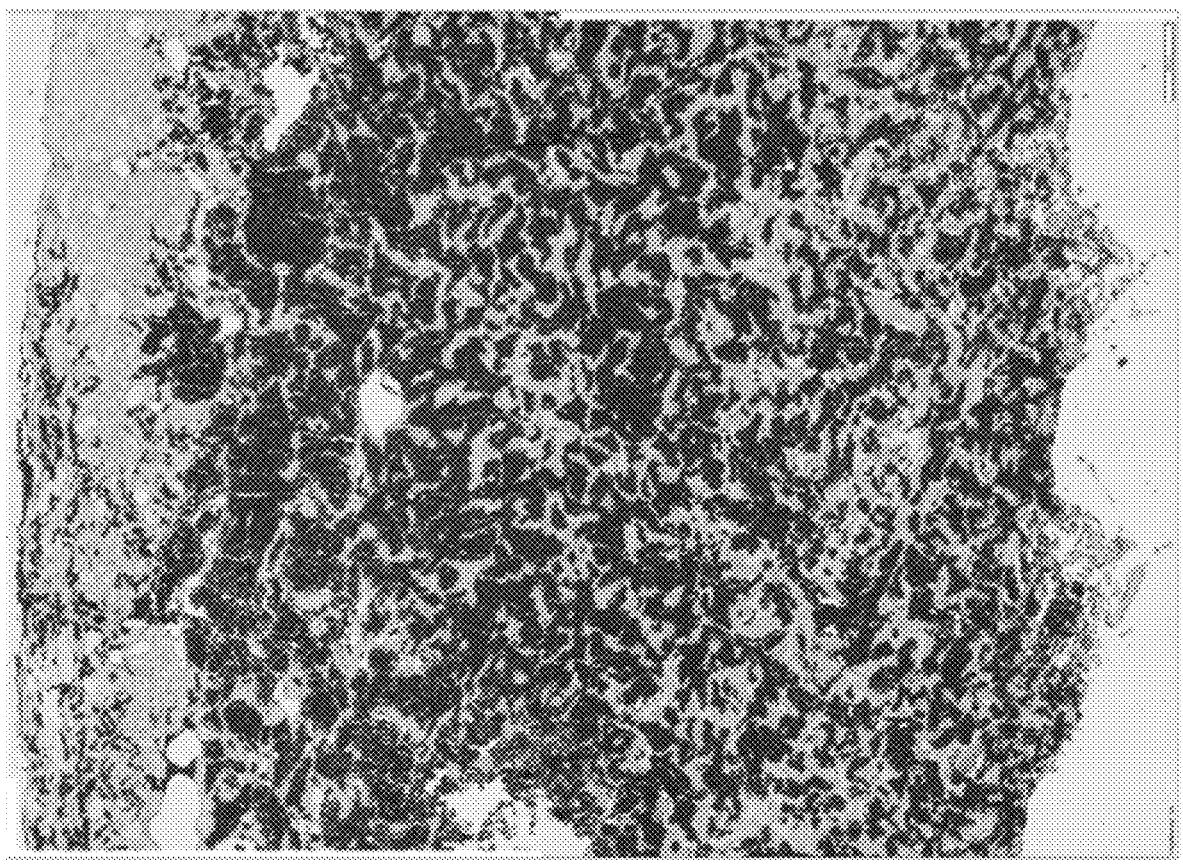
FIG. 13 shows histological staining of the multilayer sheet of collagen material of the present disclosure soaked with blood using Masson-Goldner stain (scale bar=200 μm).

The multilayer sheet of collagen material of the present disclosure were completely soaked with native human blood and samples left at room temperature. After 60 minutes, the membrane material with coagulated blood was fixed in 10% neutral-buffered formalin solution (Sigma) and processed for sectioning and histological staining. Paraffin-embedded sections were stained with standard Masson's Trichrome stain as shown in FIG. 13 (scale bar=200 µm). Red and white blood cells were detected within the collagen fibers of the porous part of the multilayer sheet of collagen material of the present disclosure.

Example 10: Chronic Ulcer Results for DFU and VLU for the Method Using the Multilayer Sheet of Collagen Material of the Invention Compared to a Method Using EpiFix®

Human patients suffering from chronic ulcers, particularly diabetic foot ulcers DFU and venous leg ulcers VLU, were treated according to the method of the present disclosure. The ulcers were photographed and characterized before implantation, soon after implantation, and during the treatment period for DFU and VLU similarly to what is shown in FIG. 3 and FIG. 4 for DFU. The method of the present disclosure successfully achieved for both DFU and VLU 80-100% closure of chronic ulcers of various sizes and in various patients within 1 to 6 weeks of implantation.

Table 1 summarizes wound closure results in DFU or VLU subjects using the method of the present disclosure:

| Study # | Number of subjects | Mean ulcer size (cm$^2$) | Mean time to closure (weeks) |
| --- | --- | --- | --- |
| 1 | 10 (DFU, Wagner grades 1-2) | 3.3 | 2.7 |
| 2 | 6 (DFU and VLU, Wagner grades 2-3) | 2.5-300 | In progress |
| 3 | 3 (VLU, Wagner grades 1-2) | 15 | 3 to 5 |
| 4 | 1 (DFU, Wagner grade 1) | 9 | ~3 |
| Control (EpiFix ® as published in Zelen et al., Int. Wound J., 2016 April; 13(2): 272-82) | 32 (DFU) | 2.6 | 3.3 |

In appropriate cases, VAC therapy was used with the multilayer sheet of collagen material of the present disclosure and it was observed that the multilayer sheet of collagen material of the present disclosure could successfully be used with VAC therapy.

Further summaries of clinical experiences are provided in Table 2:

| Patient No. | Sex | Age | Weight (lb) | Height (ft/in) | Body Mass Index (BMI) | Duration pre-existing DFU | Wagner Grade | DFU location |
|---|---|---|---|---|---|---|---|---|
| 1 | M | 64 | 223 | 6'0" | 30.2 | 10 | 1 | Plantar distal central metarsal |
| 2 | M | 81 | 273 | 6'4" | 33.2 | 4 | 1 | Plantar distal lateral metarsal |
| 3 | M | 64 | 250 | 5'11" | 47.2 | 6 | 1 | Plantar 2nd toe |
| 4 | F | 57 | 200 | 5'7" | 30.4 | 40 | 1 | Dorsal hallux toe |
| 5 | M | 43 | 280 | 6'4" | 34.1 | 8 | 2 | Plantar medial Metatarsal |
| 6 | M | 73 | 200 | 6'0" | 27.1 | 14 | 1 | Plantar medial Metatarsal |
| 7 | F | 63 | 190 | 5'4" | 32.6 | 24 | 1 | Plantar distal central metatarsal |
| 8 | M | 68 | 210 | 6'0" | 28.5 | 4 | 1 | Medial metatarsal |
| 9 | F | 75 | 200 | 5'3" | 35.4 | 8 | 1 | Plantar midfoot |
| 10 | M | 59 | 290 | 5'8" | 42.8 | 5 | 1 | Plantar midfoot |
| Mean | — | 64.7 | 231.6 | 5'8" | 34.2 | 12.3 | n.a. | — |
| SD | — | 10.6 | 38.1 | 0.4 | 6.3 | 11.5 | n.a. | — |

Patients summarized in Table 2 had failed to heal after a minimum of 4 weeks of standard wound care regimens such as collagen alginate dressings, negative pressure therapy, and off-loading. Patients had been previously treated with other wound care regimens for an average of 12.3 weeks. The protocol for this study was approved by the Western Institutional Review Board (20182784), and activities were conducted in conformance with the ethical guidelines of the Declaration of Helsinki.

Patients were instructed to off-load the limb, given a diabetic offloading boot and returned weekly for wound evaluation and dressing change. At each weekly visit, the wound area was examined to identify indicators of complications such as infection or necrosis. The wounds were photographed and measured for area using acetate tracing and 2D analysis. A new multilayer sheet of collagen material of the present disclosure was applied to non-healed wounds at each visit.

Complete healing was defined as 100% re-epithelialisation without drainage or need for dressing. The primary outcome measure was the proportion of patients healed at or before 12 weeks. The treating clinician evaluated each DFU for closure each week, and wound healing was further adjudicated by three plastic surgeons based on the acquired photographic images. The time to heal and percent ulcer area reduction were recorded for each patient. Time to heal was evaluated through Kaplan-Meier analysis using the Prism software (Prism 8, GraphPad; San Diego, Calif.).

Prior to treatment with the multilayer sheet of collagen material of the present disclosure, the mean wound size was 3.3 cm$^2$, and the mean initial wound depth was 0.3 cm. Upon application, it was observed in all instances that the multilayer sheet of collagen material of the present disclosure immediately conformed to the wound surface and absorbed wound fluid, blood, and any added saline. A direct apposition between the multilayer sheet of collagen material of the present disclosure and the wound bed was achieved, maintaining the position of the graft in the bed. During follow-up visits, the superficial dressings were easily removed without adherence to the underlying newly formed tissue. Inspection of the wounds revealed no signs of infection or necrosis in any patient at any time point. In plantar DFUs, the graft was consistently observed to be completely integrated, replaced by tissue, or resorbed at 1 week after each application, while some residual wound matrix was consistently detectable in DFU sites in the lateral, posterior, and toe locations.

Figure 14:
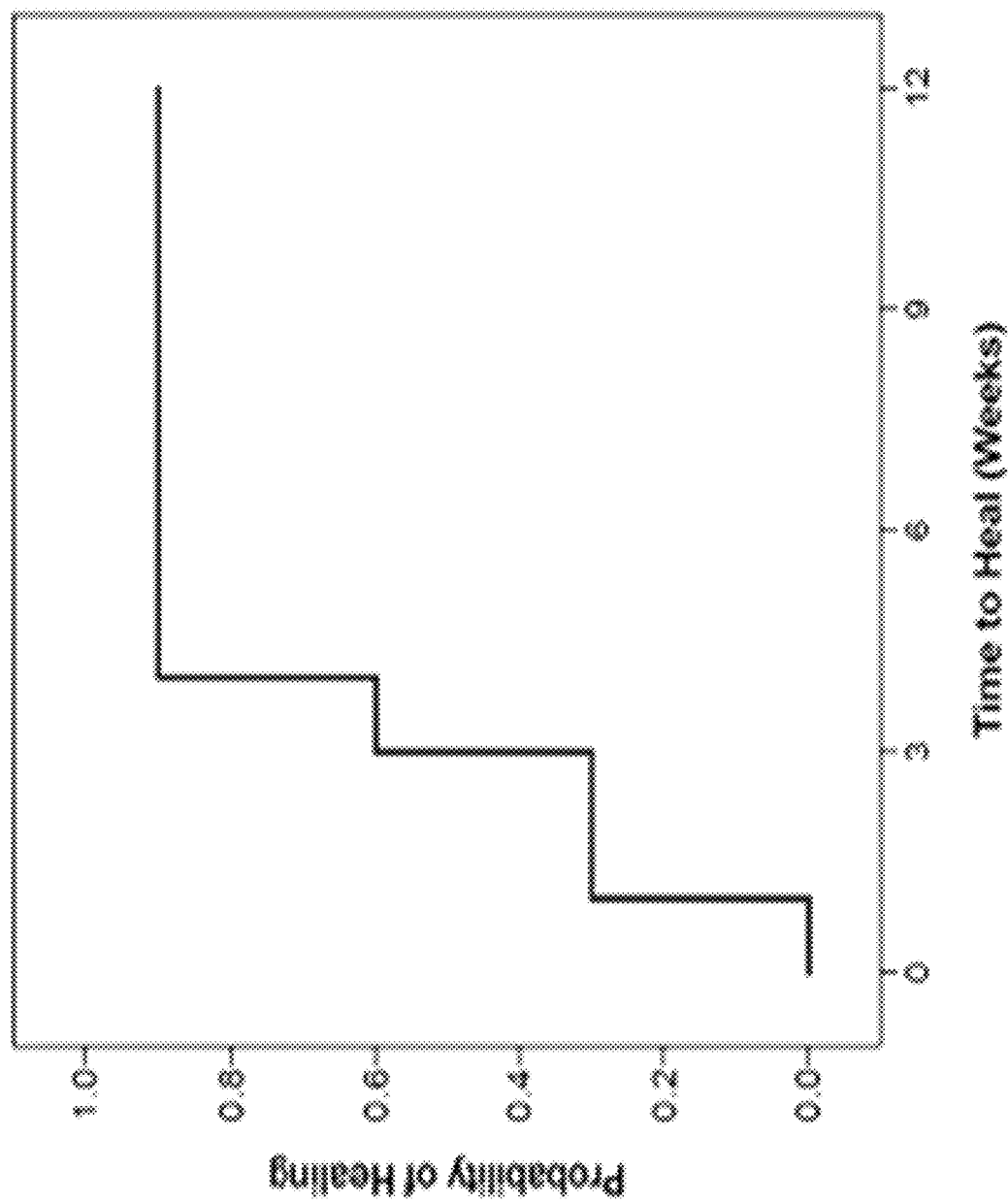
FIG. 14 shows the Kaplan-Meier plot of time to heal; 90% of patients healed within 4 weeks of initiating treatment with the multilayer sheet of collagen material of the present disclosure.
Figure 15B:
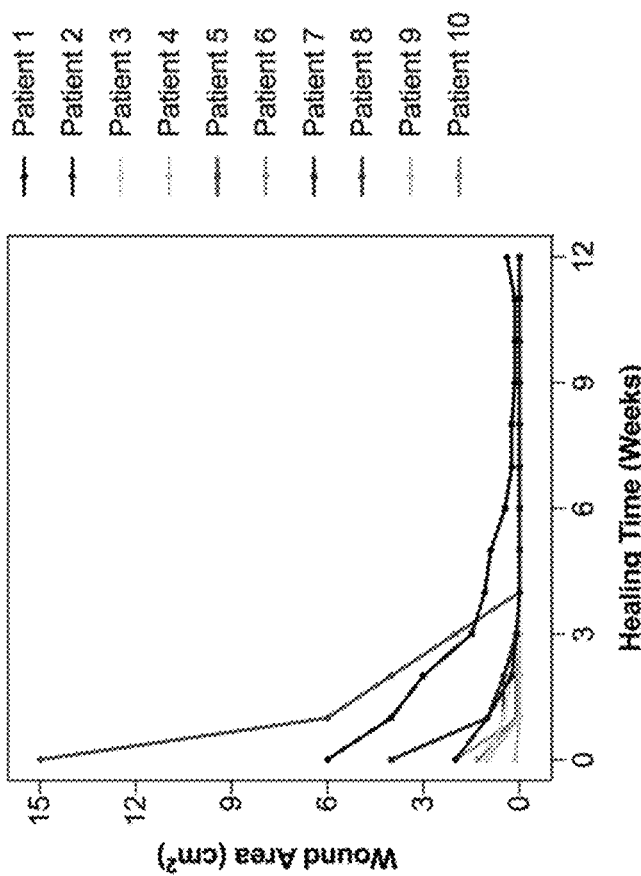
FIG. 15B shows the measured wound area by patient plotted over the 12-week treatment course with the multilayer sheet of collagen material of the present disclosure.
Figure 15A:
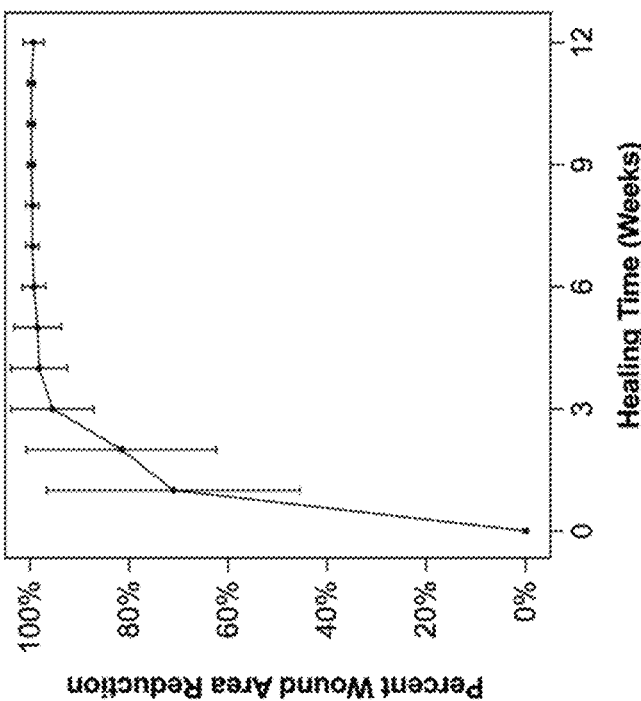
FIG. 15A shows the mean percent wound area reduction plotted over the 12-week treatment course with the multilayer sheet of collagen material of the present disclosure. Error bars represent SD.
Figure 16:
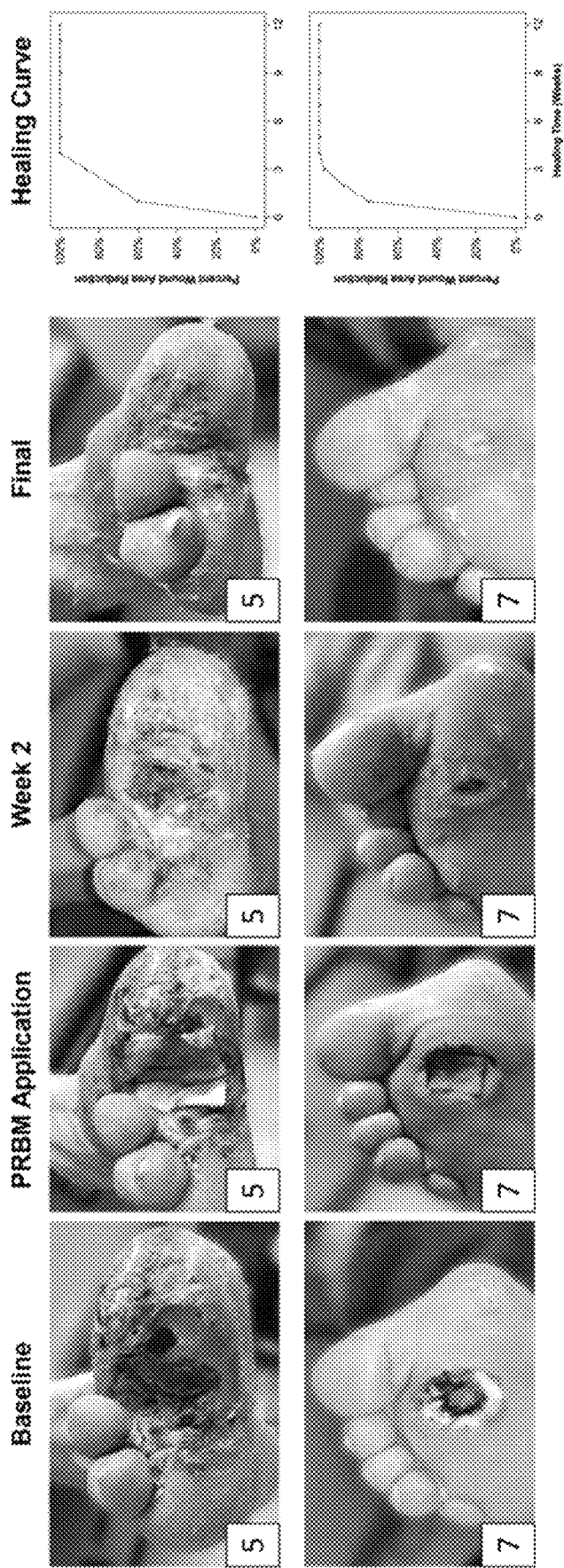
FIG. 16 is representative images of the healing time course for the two study patients with Wagner 2 wounds and their respective progression to closure during treatment with the multilayer sheet of collagen material of the present disclosure (patients 5 and 7; Table 2). The patient in the top row had the largest wound in the pilot study and healed in 4 weeks. The patient in the lower row is representative of the median, also with complete healing in 4 weeks.
Figure 17:
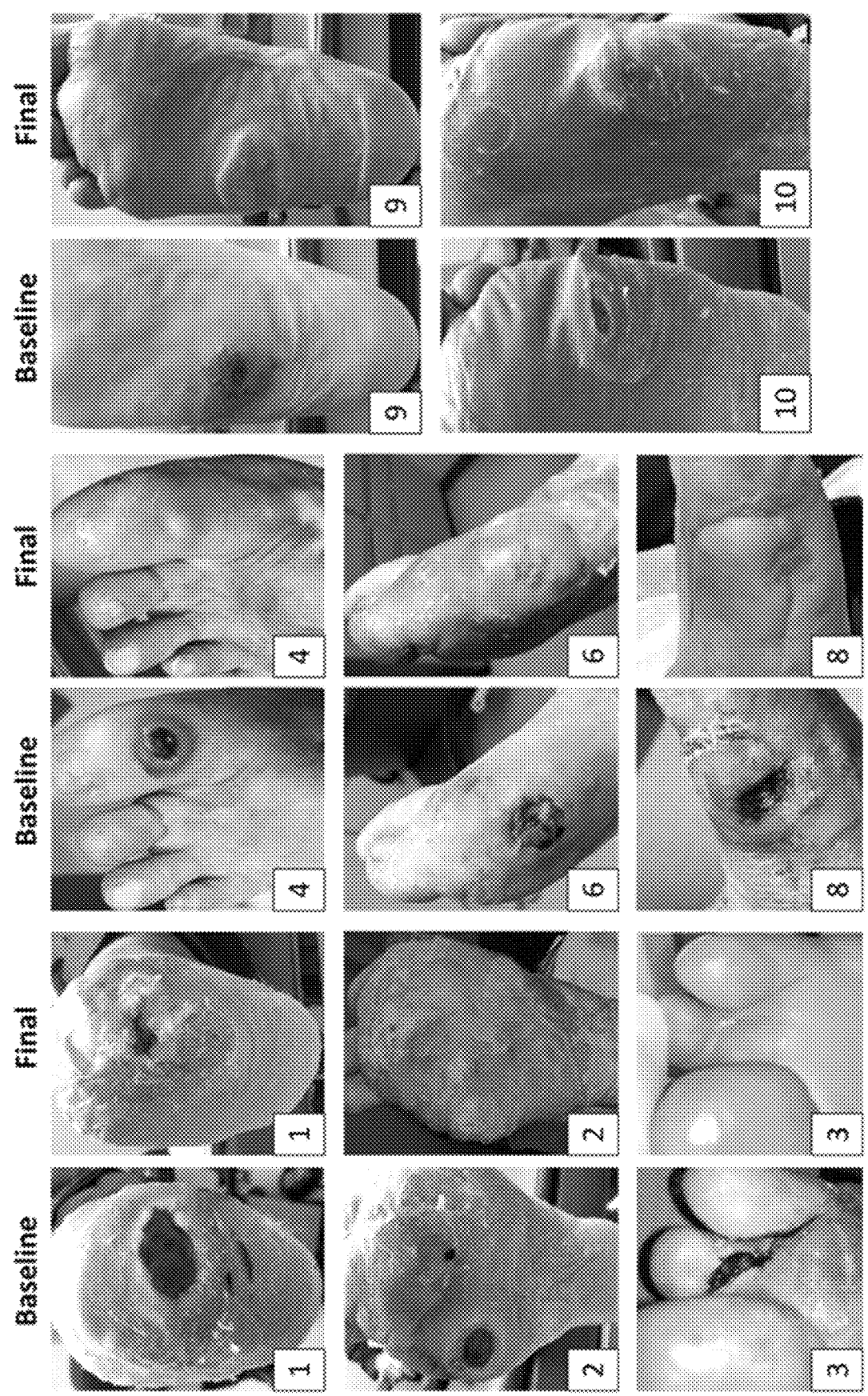
FIG. 17 is images of all Wagner 1 wounds at baseline and at closure or at 12-week study conclusion during treatment with the multilayer sheet of collagen material of the present disclosure (subjects 1-4, 6, 8-10; demographic detailed in Table 2). While patient 1 did not fully heal over 12 weeks, the ulcer was substantially reduced in size during the treatment period.

Wound closure was observed in 9 of 10 patients (90%) by the conclusion of the 12-week period with a mean time to closure of 2.7 weeks (FIG. 14). Complete closure was achieved at 1 week in 3 patients, at 3 weeks in 3 patients, and at 4 weeks in 3 patients. In summary, nine of 10 DFUs healed within 4 weeks after beginning treatment. Notably, after 1 week, the mean wound area reduction was 71±26%. Further incremental wound area reduction was observed at 4 weeks (98±6%) and 6 weeks (99±2%) (FIGS. 15A and 15B). At the 12-week study endpoint, the mean wound area reduction for all 10 patients was 99±2% (FIG. 15A). Both Wagner 2 wounds healed over the study period (FIG. 16). Seven out of eight of the Wagner 1 wounds healed (FIG. 17).

Those early clinical experiences showed that for both DFU and VLU ulcer closure times and rates were comparable with or better than the reported closure rates and times for the significantly more expensive and difficult-to-handle advanced wound care product EpiFix®. Moreover, the multilayer sheet of collagen material of the present disclosure integrated with regenerated tissue at the chronic ulcer site without causing excessive inflammation or dehiscence.

Example 11: Clinical Study in Progress Comparing for DFU Treatment the Method of the Invention Using the Multilayer Sheet of Collagen Material to a Method Using a Conventional Wound Care Product A prospective, multi-center, parallel group randomized controlled clinical trial is conducted to compare treatment of patients suffering from diabetic foot ulcers with the multilayer sheet of collagen material of the present disclosure in comparison to Fibracol® (collagen plus alginate wound care product). Fibracol® has been commonly used as a standard treatment for diabetic foot wounds for over 15 years.

Human patients that are at least 18 years old and have a diabetic foot ulcer, Wagner grade 1, extending at least through the dermis and present for greater than 4 weeks and less than 1-year, wherein the ulcer is a minimum of 1.0 cm$^2$ and a maximum of 25 cm$^2$ are included in the trial.

The affected DFU site is prepared in accordance with the present disclosure and the multilayer sheet of collagen material of the present disclosure or Fibracol is implanted into the DFU site. The study design for the comparative trial is appropriately in line to be able to compare standard therapy to the inventive therapy at 12 weeks, which is the standard time to evaluate for complete closure.

The primary endpoint of the study is the percentage of DFU healed at 12 weeks. Secondary endpoints include the percentage of index ulcers healed at 6 weeks, the time to heal within 6 and 12 weeks, the percent Area Reduction (PAR) at 6 and 12 weeks, changes in peripheral neuropathy, changes in wound quality of life (per W-QoL), to remove bacteria and other pathogens at 12 weeks, need for measures to control bleeding, product wastage, and cost to ulcer closure. Complete closure is defined as 100% re-epithelialization without drainage.

It is expected that the primary end point and one or more of the secondary endpoints will be significantly higher/improved using the multilayer sheet of collagen material of the present disclosure compared to using Fibracol®.

Interim results from the clinical trial have been obtained. It was found that in the patients treated with the multilayer sheet of collagen material of the present disclosure, 14/19 healed, 2/19 failed, and 3/19 have not yet completed the study treatment period. In the standard of care group, 5/16 healed, 9/16 failed, and 2/16 have not yet completed the study treatment period.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method of treating a chronic skin ulcer in a subject in need thereof, comprising:
   i) cleaning to remove bacteria and other pathogens and/or debriding the chronic skin ulcer until the edges of the ulcer contain viable tissue;
   ii) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that the rough fibrous face of said barrier layer of collagen material to which is connected said spongeous matrix layer of collagen material having an open sponge-like texture, faces toward and is adjacent to the bed of the chronic skin ulcer;
   iii) hydrating the implanted multilayer sheet of collagen material in dry state using blood, an isotonic solution or a combination thereof; and
   iv) providing a dressing over the implanted, hydrated multilayer sheet of collagen material, thereby restarting stalled cell migration, proliferation and angiogenesis at the chronic skin ulcer site.

2. The method of claim 1, wherein the collagen of said barrier layer of collagen material is predominantly collagen I, collagen III or a mixture thereof.

3. The method of claim 1, wherein said the collagen of said spongeous matrix layer of collagen material is predominantly collagen I, collagen III or a mixture thereof.

4. The method of claim 1, wherein multilayer sheet of collagen material has a thickness of about 0.5-25 mm.

5. The method of claim 1, wherein the chronic ulcer extends at least through the dermis and has been present for greater than 4 weeks.

6. The method of claim 1, wherein the chronic ulcer extends at least through the hypodermis and has been present for greater than 6 weeks.

7. The method of claim 1, further comprising applying a secondary dressing or re-dressing the chronic ulcer after step iv) is performed.

8. The method of claim 1, further comprising applying sterile saline to remove a dressing material from the multilayer sheet of collagen material after step iv) is performed.

9. The method of claim 1, further comprising changing the dressing over the implanted multilayer sheet of collagen material every 1 to 7 days after step iv) is performed.

10. The method of claim 1, further comprising removing exudate from the chronic ulcer site every 1 to 7 days after step iv) is performed.

11. The method of claim 1, further comprising inspecting the chronic ulcer every 1 to 7 days after step iv) and removing the dressing after a first visible epithelialization is observed at the chronic ulcer or removing the implanted multilayer sheet of collagen material and repeating steps i) to iv) if one or more of redness, swelling, hematomas, blistering, inflammation, excess exudate, infection, and necrosis are observed at the chronic ulcer.

12. The method of claim 1, further comprising performing one or more of toe-blood pressure readings, pulse volume recordings, transcutaneous oxygen measurements, and skin perfusion pressure measurements.

13. The method of claim 1, further comprising one or more of promoting neutrophils and monocytes to localize at the chronic ulcer site, promoting formation of a multilayered cell structure in the ulcer site, promoting conversion of monocytes to macrophages, promoting secretion of the patient's own growth factors, promoting tissue proliferation and cell migration, promoting production and cross-linking of collagen at the chronic ulcer site, promoting growth of endothelial cells, promoting angiogenesis that was stalled at the chronic ulcer site, promoting formation of a vascular network and granulation, promoting oxygenation of the chronic ulcer site, and reducing one or more of purulent drainage, erythema, pain, warming, tenderness, induration, and bleeding at the chronic ulcer site.

14. A method of increasing liquid uptake capacity in a chronic skin ulcer of a subject in need thereof, comprising:
   i) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic skin ulcer; and
   ii) hydrating the multilayer sheet of collagen material in dry state using blood, an isotonic solution or a combination thereof, thereby increasing liquid uptake capacity in the chronic skin ulcer.

15. The method of claim 14, further comprising inhibiting exudate drainage, bleeding from the chronic ulcer, and preventing floating away of the multilayer sheet of collagen material out of the bed of the chronic ulcer.

16. A method of promoting hemostasis in a chronic skin ulcer of a subject in need thereof, comprising:

i) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic skin ulcer; and ii) hydrating the implanted multilayer sheet of collagen material using blood, an isotonic solution or a combination thereof, thereby promoting hemostasis in the chronic skin ulcer.

17. The method of claim 16, wherein blood clot formation in a chronic ulcer is accelerated by at least 2-fold compared to blood clot formation in a chronic ulcer in the absence of said implanted multilayer sheet of collagen material.

18. A method of binding and preserving a subject's growth own factors in a chronic skin ulcer of a subject in need thereof, comprising:

i) aseptically implanting into the chronic skin ulcer of the subject a multilayer sheet of collagen material in dry state comprising (a) a barrier layer of collagen material having a smooth face and a rough fibrous face opposite said smooth face and (b) a spongeous matrix layer of collagen material connected to said rough fibrous face, said spongeous matrix layer of collagen material having an open sponge-like texture, such that said rough fibrous face of said barrier layer of collagen material to which is connected said spongeous matrix layer of collagen material having an open sponge-like texture faces toward and is adjacent to the bed of the chronic ulcer; and ii) hydrating the implanted multilayer sheet of collagen material using blood, an isotonic solution or a combination thereof, thereby promoting binding of said subject's own growth factors with the multilayer sheet of collagen material and preservation of said subject's own growth factors and growth factor activity in the chronic skin ulcer thereby inducing expression of one or more growth factor-responsive genes in one or more human cell types in the chronic skin ulcer of the subject.

19. The method of claim 18, wherein the growth factors are two or more of transforming growth factors (TGFs), fibroblast growth factors (FGFs), epidermal growth factor (EGF), Insulin-like Growth Factor (IGF-1), Platelet-derived Growth Factors (PDGFs), and vascular endothelial growth factors (VEGFs).

20. The method of claim 18, wherein said one or more human cell types are human fibroblasts, human epidermal keratinocytes, human endothelial cells and human pluripotent stem cells.

21. The method of claim 1, further comprising attracting one or more human cell types to the chronic skin ulcer, wherein said one or more human cell types are human fibroblasts, human epidermal keratinocytes, human endothelial cells and human pluripotent stem cells.

22. The method of claim 1, further comprising promoting attachment and growth of one or more human cell types in the chronic skin ulcer, wherein said one or more human cell types are human fibroblasts, human epidermal keratinocytes, human endothelial cells and human pluripotent stem cells.

23. The method of claim 1, further comprising inhibiting one or more MMPs in the chronic skin ulcer, wherein the MMPs are a plurality of MMP-1, MMP-2, MMP-3, MMP-8, and MMP-9.

24. The method of claim 1, wherein the subject suffers from diabetic foot ulcer (DFU) or venous leg ulcer (VLU).

25. The method of claim 1, wherein the subject has been or is being treated with corticosteroid therapy, is undergoing radiation therapy, is receiving anti-coagulation therapy, chemotherapy, or uses drugs, alcohol, tobacco, or other agents that disrupt a normal ulcer healing process.

26. The method of claim 1, further comprising treating the subject with compression therapy, vacuum assisted closure (VAC), offloading, negative pressure, hyperbaric oxygen therapy, or a combination thereof.

27. The method of claim 1, wherein the multilayer sheet of collagen material in dry state has physical properties such that it absorbs about 7 to about 12 times its weight of biological fluids.

28. The method of claim 1, wherein the multilayer sheet of collagen material has not been artificially cross-linked, has not had any growth factors or other ulcer-treating agents added to it, and/or has not had any antimicrobial agents added to it.

29. The method of claim 1, further comprising, after 4 to 7 days, removing at least a portion of the implanted multilayer sheet of collagen material and repeating the method steps.

30. The method of claim 1, further comprising providing a pH of or about 3.5 to about 6.5 in the chronic ulcer site.

* * * * *